United States Patent
Dhawale et al.

(10) Patent No.: US 7,734,331 B2
(45) Date of Patent: Jun. 8, 2010

(54) SYSTEMS, METHODS AND APPARATUS FOR PREPARATION, DELIVERY AND MONITORING OF RADIOISOTOPES IN POSITRON EMISSION TOMOGRAPHY

(75) Inventors: Paritosh Jayant Dhawale, Menomonee Falls, WI (US); Mark Alan Jackson, Menomonee Falls, WI (US); Hernan Rodrigo Lara, Milwaukee, WI (US); Michael Brussermann, Nordrhein-Westfalen (DE); Ulrich Ketzscher, Nordrhein-Westfalen (DE)

(73) Assignee: General Electric Company, Schenectady, NY (US)

( * ) Notice: Subject to any disclaimer, the term of this patent is extended or adjusted under 35 U.S.C. 154(b) by 1381 days.

(21) Appl. No.: 10/792,029

(22) Filed: Mar. 2, 2004

(65) Prior Publication Data

US 2010/0121184 A1 May 13, 2010

(51) Int. Cl.
 *A61B 6/00* (2006.01)
 *A61M 5/00* (2006.01)
(52) U.S. Cl. .................. 600/431; 600/436; 600/432
(58) Field of Classification Search .......... 600/431, 600/425, 436, 34; 702/19; 422/159
 See application file for complete search history.

(56) References Cited

U.S. PATENT DOCUMENTS

| | | | | |
|---|---|---|---|---|
| 4,562,829 | A * | 1/1986 | Bergner | 600/4 |
| 4,585,009 | A * | 4/1986 | Barker et al. | 600/432 |
| 4,585,941 | A * | 4/1986 | Bergner | 250/363.02 |
| 5,037,602 | A * | 8/1991 | Dabiri et al. | 376/198 |
| 5,082,980 | A * | 1/1992 | Berridge | 568/917 |
| 5,223,434 | A * | 6/1993 | Kanno et al. | 436/56 |
| 5,425,063 | A * | 6/1995 | Ferrieri et al. | 376/195 |
| 5,494,036 | A | 2/1996 | Uber, III et al. | |
| 5,569,181 | A * | 10/1996 | Heilman et al. | 604/30 |
| 5,840,026 | A * | 11/1998 | Uber et al. | 600/431 |
| 5,843,037 | A * | 12/1998 | Uber, III | 604/151 |
| 5,885,216 | A * | 3/1999 | Evans et al. | 600/431 |

(Continued)

FOREIGN PATENT DOCUMENTS

EP 0 310 148 A 4/1989

(Continued)

OTHER PUBLICATIONS

Satyamurthy, N. et al. "Electric Generators for the Production of the Positron-Emitter Labeled Radiopharmaceuticals: Where Would PET Be Without Them?" Clinical Positron Imaging. vol. 5, No. 5: 233-253, 1999.*

(Continued)

*Primary Examiner*—Eric F Winakur
*Assistant Examiner*—Helene Bor
(74) *Attorney, Agent, or Firm*—Dean Small; Small Patent Law Group

(57) ABSTRACT

In one aspect, systems, methods and apparatus are provided through which a dispensing station dispenses a large quantity of a radiotracer to one or more positron emission tomography imaging stations. In some aspects a quality control unit verifies the quality of the radiotracer. In some embodiments, components of the system are coupled by a local area network. In some aspects, each positron emission tomography imaging station includes an injector system, a physiological monitoring device, and a positron emission tomography scanner. All of the devices can be controlled by a computer system.

90 Claims, 12 Drawing Sheets

U.S. PATENT DOCUMENTS

| | | | |
|---|---|---|---|
| 5,917,874 A * | 6/1999 | Schlyer et al. | 376/194 |
| 5,920,054 A * | 7/1999 | Uber, III | 235/375 |
| 5,932,178 A * | 8/1999 | Yamazaki et al. | 422/159 |
| 6,011,825 A * | 1/2000 | Welch et al. | 376/195 |
| 6,442,418 B1 * | 8/2002 | Evans et al. | 600/431 |
| 6,444,990 B1 * | 9/2002 | Morgan et al. | 250/398 |
| 6,520,930 B2 * | 2/2003 | Critchlow et al. | 604/67 |
| 6,567,492 B2 * | 5/2003 | Kiselev et al. | 376/195 |
| 6,643,537 B1 | 11/2003 | Zatezalo et al. | |
| 6,704,592 B1 * | 3/2004 | Reynolds et al. | 600/411 |
| 6,741,881 B2 * | 5/2004 | Prince | 600/420 |
| 6,767,319 B2 * | 7/2004 | Reilly et al. | 600/5 |
| 6,870,175 B2 * | 3/2005 | Dell et al. | 250/506.1 |
| 6,879,853 B2 * | 4/2005 | Meaney et al. | 600/420 |
| 6,889,072 B2 * | 5/2005 | Prince | 600/420 |
| 6,889,074 B2 * | 5/2005 | Uber et al. | 600/431 |
| 7,200,198 B2 * | 4/2007 | Wieland et al. | 376/195 |
| 7,204,797 B2 * | 4/2007 | Reilly et al. | 600/5 |
| 2003/0004463 A1 | 1/2003 | Reilly et al. | |
| 2003/0216609 A1 * | 11/2003 | Dell et al. | 600/34 |
| 2004/0088188 A1 * | 5/2004 | Hamadeh et al. | 705/2 |
| 2004/0195512 A1 * | 10/2004 | Crosetto | 250/363.04 |
| 2004/0258615 A1 * | 12/2004 | Buchanan et al. | 424/1.11 |
| 2005/0085682 A1 * | 4/2005 | Sasaki et al. | 600/4 |
| 2005/0107697 A1 * | 5/2005 | Berke | 600/431 |
| 2005/0203389 A1 * | 9/2005 | Williams | 600/431 |
| 2005/0232387 A1 * | 10/2005 | Padgett et al. | 376/194 |
| 2005/0276751 A1 * | 12/2005 | Chao et al. | 424/1.11 |
| 2005/0277833 A1 * | 12/2005 | Williams, Jr. | 600/431 |
| 2005/0288869 A1 * | 12/2005 | Kroll et al. | 702/19 |
| 2006/0074306 A1 * | 4/2006 | Greathouse | 600/431 |
| 2006/0104401 A1 * | 5/2006 | Jongen et al. | 376/190 |
| 2007/0157931 A1 * | 7/2007 | Parker et al. | 128/204.23 |
| 2008/0091142 A1 | 4/2008 | Trombley, III et al. | |
| 2008/0166292 A1 | 7/2008 | Levin et al. | |

FOREIGN PATENT DOCUMENTS

EP   542565 A1 *   5/1993

OTHER PUBLICATIONS

Rodney Huddleston et al. Cambridge Grammar of the English Language. New York : Cambridge University Press, 2002.*

* cited by examiner

SYSTEMS, METHODS AND APPARATUS FOR PREPARATION, DELIVERY AND MONITORING OF RADIOISOTOPES IN POSITRON EMISSION TOMOGRAPHY

RELATED APPLICATION

This application is related to copending U.S. application Ser. No. 10/792,683, filed Mar. 2, 2004 entitled "Systems, methods and apparatus for infusion of radiopharmaceuticals."

FIELD OF THE INVENTION

This invention relates generally to positron emission tomography, and more particularly to positron emission tomography control systems.

BACKGROUND OF THE INVENTION

In conventional positron emission tomography control systems, an individual dose of a premeasured radiotracer is administered to an individual patient. The individual premeasured radiotracer is prepared by a radiotracer supplier (commonly called a radiopharmacy). A Cyclotron is used most commonly to prepare the radiotracer. The radiotracer is delivered to a medical facility that administers the individual premeasured radiotracer as a radiopharmaceutical. The individual premeasured radiotracer is prepared by the radiotracer supplier in accordance with a prescription from a physician. The prescription includes a prescribed amount of radioactivity at a future time and a date of the prescribed administration in a known volume of a liquid suitable for injection into a living subject.

The conventional process of radiotracer production in a cyclotron performed by a radiotracer supplier is as follows: The radiotracer supplier irradiates a target material in the cyclotron with a beam of protons or deuterons to produce a desired amount of radioactivity in the target material. The extent of irradiation is planned to fulfill the need of radioactivity at the prescribed future time and date. The irradiated target material is a radioisotope. Examples of cyclotron produced radioisotopes include nitrogen-13, fluorine-18, carbon-11 and oxygen-15. Often, compounds are bond to the radioisotope to produce radiotracers such as fluorodeoxyglucose (FDG) which is produced using fluorine-18. Other radiotracers include nitrogen-13 ammonia which is used in myocardial applications, carbon-11 tracers which are commonly used in neurologic applications; and oxygen-15 gas as well as tracers derived from it which are commonly used in blood flow applications. FDG is by far the most commonly used radiotracer and has a half life of 109 minutes allowing for its distribution from a centralized radiopharmacy to multiple imaging sites.

Typically the radiotracer supplier packages the radiotracer in an individual dose vial such as in the case of FDG. Thereafter, the individual dose vial is packaged in an individual lead-shielded container. Each lead-shielded container weighs approximately 50-60 lbs. Typically, the radiotracer supplier will prepare a number of individual dose vials for each medical facility each day. Each of the dose vials are packaged in an individual container. As a result, a number of 50-60 lb containers will be delivered to each medical facility each day. Furthermore, in order to accommodate unplanned changes in the needs of radiotracer by a medical facility, as well as to meet other logistical needs, conventionally two or more deliveries of individual dose vials in individual containers will be made each day. The two or more deliveries are typically performed in the early morning before 7 am, and in the late morning between 10 am and 11 am, or as desired by the medical facility. The cost and overhead of preparing individual dose vials, packaging and transporting a number of the heavy containers twice a day is significant.

In addition, when the radiopharmaceutical is administered to the patient, the PET technician is exposed to radioactivity. The PET technician connects an intravenous tube (IV) into the radiopharmaceutical container, inserts a needle at the other end of the IV into the patient, starts the infusion of the radioisotope through the IV, monitors the progress of the infusion, and ends the infusion, all the while remaining close-by the patient and the IV containing the radiopharmaceutical. This close proximity to the radioactivity results in numerous low levels of exposure to radioactivity that can be harmful to the health of the PET technician.

Quality control of the amount of radionuclic and chemical purity of the bulk batch is typically performed under manual direction and control by the supplier. As a result of the manual aspects of the quality control, the standards of quality control are subjective. Furthermore, conventional systems can be slow, which requires that the radioisotope material must be produced at a much stronger level of radioactivity in order to have the required amount of radioactivity at the time of injection.

A number of radioisotopes have such short half-lives, that the radioisotope must be produced by a cyclotron in close proximity to the medical facility. Nitrogen-13 ammonia has a half-life of 10 minutes, and oxygen-15 has a half-life of 2.1 minutes. Due to its short half-life, nitrogen-13 ammonia and oxygen-15 necessitate production in close proximity to the medical facility site. Therefore, the use of nitrogen-13 ammonia and oxygen-15 for PET is limited to those sites that have immediate access to its production.

More generally, conventional systems are sequential and step wise. Major functions, such as the production of the radiotracer, and the injection of the radiopharmaceutical, collection of clinical data following a specific imaging protocol, are managed by separate organizations, by different personnel, often in a somewhat uncoordinated and disjoint manner.

For the reasons stated above, and for other reasons stated below which will become apparent to those skilled in the art upon reading and understanding the present specification, there is a need in the art to reduce the number of individual dose vials and shielded containers that radioisotope suppliers prepare and deliver to each medical facility each day. There is also a need to reduce the number of delivery trips that a radiotracer supplier makes to each medical facility each day. In addition, there is a need to reduce the exposure of people, such as PET technicians, to radioactivity during the manual steps of administering a radiopharmaceutical to patients. There is also a need to improve the quality control of the administration of radiopharmaceuticals to patients. Moreover, there is a need to reduce the disjoint management and control of the functions of preparing and injection radioisotopes into patients. Furthermore, there is a need to provide a convenient method for on-site production and administration of nitrogen-13 ammonia radiopharmaceutical for cardiac studies.

BRIEF DESCRIPTION OF THE INVENTION

The above-mentioned shortcomings, disadvantages and problems are addressed herein, which will be understood by reading and studying the following specification.

In one aspect, a system includes a local area network that is operably coupled to one or more positron emission tomography imaging systems. The system also includes a dispensing station that is operable to receive a multidose portion or vial of a radiopharmaceutical. The dispensing station is operable to dispense portions of the radiopharmaceutical to the one or more positron emission tomography imaging system. The dispensing station is also operably coupled to the local area network. The dispensing station dispenses a radiopharmaceutical in the patients who are subsequently imaged using the positron emission tomography imaging systems. The dispensing station allows a multidose portion of the radiopharmaceutical to be dispensed to the patients, which provides economies of scale and a convenient way of distribution of the radiopharmaceutical.

In another example, the system also includes a quality control unit. The quality control unit is operable to monitor the radiochemical and the radionuclic purity of the radiopharmaceutical that is dispensed by the dispensing station. The quality control unit is operably coupled to the local area network and operably coupled to the dispensing station.

In still another example, a chemical synthesizer is operably coupled between a radioisotope producer, (e.g. a cyclotron, a linear accelerator or a radioisotope generator) and the dispensing station. The synthesizer receives a radioisotope from the radioisotope producer, bonds the radioisotope to a biological compound, and transfers the resulting radiotracer to the dispensing station.

In yet another example, the apparatus includes a control system that is operably coupled to the local area network, to receive status information from, and send commands to, any one of the device in the system, such as the one or more positron emission tomography imaging systems, the dispensing station, the chemical synthesizer and the quality control unit. The control system determines an amount of radioactivity and an amount of radioisotope to produce and sends instructions to the radioisotope producer accordingly.

In some examples, a positron emission tomography imaging system includes an injector system, a physiologic monitor operably coupled to the injector, and a positron emission tomography scanner operably coupled to the physiologic monitor and the injector. The injector is operable to receive multiple doses of the radiopharmaceutical and operable to inject individual doses of the radiopharmaceutical into a patient, initiate scanning at a predefined time following a specific predefined clinical protocol. The injector is also capable of injecting other pharmaceuticals as defined in the protocol.

In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is presented. In the second section, apparatus of an embodiment are provided. In the third section, methods of embodiments are provided. The fourth section, the hardware and the operating environment in conjunction with which embodiments may be practiced are described. In the fifth section, a conclusion of the detailed description is provided.

System Level Overview

Figure 1:
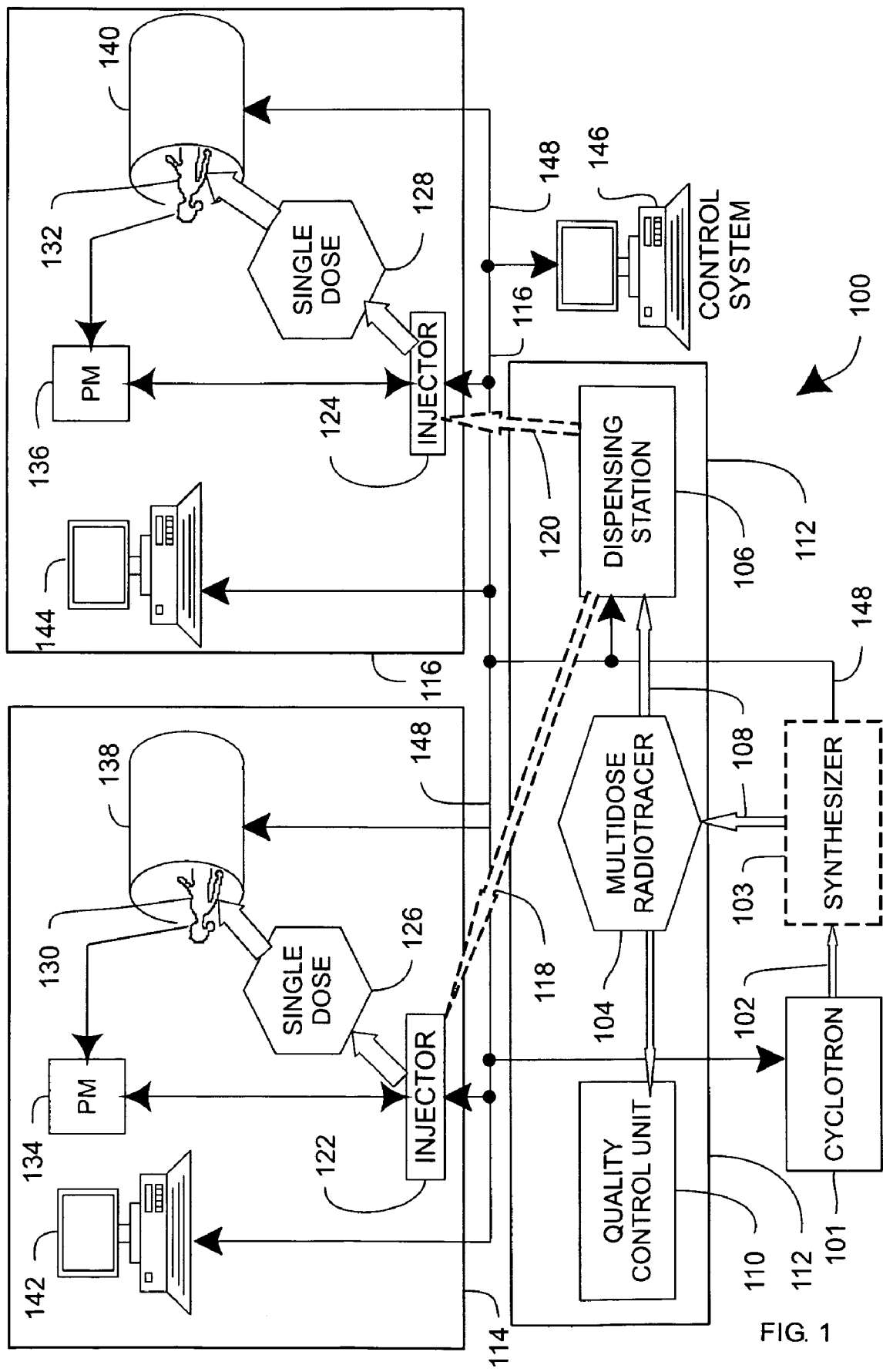
FIG. 1 is a diagram illustrating a system-level overview of an embodiment.

FIG. 1 is a block diagram that provides a system level overview of a medical radiopharmaceutical administration system 100. The medical radiopharmaceutical administration system 100 is an integrated system for production, quality control and distribution of medical radiopharmaceuticals in positron emission tomography (PET) imaging.

System 100 includes a cyclotron 101. The cyclotron 101 irradiates a target material with radiation, producing a radioisotope 102. Multiple doses of the radioisotope 102 are produced by the cyclotron 101. Other examples of devices that produce radioisotopes include linear accelerators (LINIACs) and radioisotope generator. Rubidium-82 is produced by a radioisotope generator. In some embodiments, the radioisotope 102 is chemically bonded to a biological compound in a chemical synthesizer 103, producing a radiotracer 104.

The multidose portion of radioisotope 102 or radiotracer 104 is transferred to a dispensing station 106. In embodiments where the radiotracer 104 or radioisotope 102 have a short half life (e.g. carbon-11, oxygen-15 and nitrogen-13), the transfer is performed through a line that shields radioactivity, such as a lead-shielded line 108 as shown in FIG. 1. In embodiments where the radiotracer 104 or radioisotope 102 has a longer half life (e.g. flourine-18) the transfer may be performed by placing the multidose portion of radioisotope 102 or radiotracer 104 in a reservoir and transporting the reservoir to the dispensing station 106 and emptying the contents of the reservoir in the dispensing station 106.

Regardless of how the material is transported, the multidose portion of radioisotope 102 or radiotracer 104 is stored in the dispensing station 106.

In some embodiments, system 100 also includes a quality control unit (QC) 110 that monitors the amount of radioactivity and other measures of quality and quantity of the multidose portion of radioisotope that is stored in the dispensing station 106. QC 110 allows the radionucleic and chemical purity, that being the quality of the radioisotope in terms of the amount of radioactivity of desired isotope, and chemical purity of the radiotracer, to be verified. In some embodiments quality control monitoring, analysis and verification is performed at particular time intervals or for particular production batches or for one representative sample of bulk produced radiotracer. The time intervals and batches can be predetermined and modified by an operator. As a result, QC 110 allows the quality control functions to be performed by an automated process which is more efficient, provides less occupational exposure, and more reliable than conventional systems. Thus, system 100 improves the quality control of the administration of radiopharmaceuticals to patients. In a system that produces and distributes nitrogen-13 ammonia, the QC 110 may still be present but may be used only on some predefined productions.

In some embodiments, the QC 110 includes a high-performance liquid chromatography (HPLC) device and/or a NaI detector. In some embodiments, QC 110 also includes a filter for the multidose portion of radioisotope that is stored in the dispensing station 106. As a result, QC 110 provides QC and filter functions that are automated, which is more convenient and more reliable than conventional systems.

In the embodiment shown in FIG. 1, the QC 110 samples multidose radiotracer 104 from the dispensing station 106. In other embodiments, the QC 110 samples multidose radiotracer 104 from a cyclotron target in the cyclotron 101. In some additional embodiments, the QC 110 estimates the amount of radioactivity in the radiotracer 104 using a calculation based on the half-life of the radiotracer 104 and the amount of time that has lapsed since the production of the radiotracer 104.

In some embodiments, system 100 includes one or more radiation shields 112 that surround portions of the system that are radioactive. The radiation shielding 112 typically includes lead. The radiation shielding 112 protects all individuals from radiation, and in particular, the radiation shielding 112 protects personnel that operate the cyclotron 101, dispensing station 106.

From the dispensing station 106, multidose portions of radiotracer 104 are dispensed to one or more PET imaging systems 114 and 116. In some embodiments, the transfer or transportation of the multidose portions of radiotracer 104 to the PET imaging systems 114 or 116 is performed through a line, 118 or 120, such as lead-shielded lines that shield radioactivity. In other embodiments, the multidose portions of radiotracer 104 is transferred or transported by placing the multidose portion of radiotracer 104 in a reservoir and transporting the reservoir to the PET imaging systems 114 and 116.

Each of the PET imaging systems 114 and 116 include an injector system 122 and 124 respectively One implementation of the injector systems 122 or 124 is discussed in more detail in FIG. 4 below. Injector systems 122 and 124 extract individual doses 126 and 128 of a radiopharmaceutical prepare, and inject or deliver, the dose into living subjects 130 and 132, respectively. In some embodiments, the living subjects 130 and 132 are human patients. Thus, system 100 allows a multidose portion of radiotracer 104 to be dispensed as individual doses 126 and 128. In comparison to conventional systems that require irradiation and shipment of many individual doses of radiopharmaceutical, preparation and shipment of a multidose portion of radiotracer 104 by system 100 is more convenient. System 100 also offers a more automated process that is more reliable than conventional systems that require more human operation. Furthermore, system 100 reduces unwanted radiation exposure to the staff.

In some embodiments, a physiologic monitoring device (PM) 134 and 136 is operably coupled to the injector system 122 and 124 and to the living subjects 130 and 132, respectively. The PMs 134 and 136 monitor a number of measures of the health of the living subject, such as blood pressure and heart activity as represented by an electrocardiogram (EKG). The PMs 134 and 136 detect abnormalities in the measures of the health of the living subject and provide notice of the abnormalities to the control system as well to clinical staff.

Each PET imaging system 114 and 116 also includes a PET scanner 138 and 140, respectively. Each PET imaging system may have one or more scanners.

The living subject 130 and 132 is placed inside the scanner 138 and 130 after or during injection of the radiopharmaceutical 126 and 128 to detect the radioactivity of the injected radiopharmaceutical 126 and 128 in the living subject 130 and 132, respectively.

A computer with a graphical user interface (GUI) 142 and 144 is located at the PET imaging system 114 and 116. A PET technician operates the computer GUI 142 and 144 in order to control, manage and oversee the entire PET process, including activities of the injector system, such as dispensing and injection of the individual dose of radiopharmaceutical 126 and 128 into the living subject 130 and 132 and scanning the living subject using appropriate clinical protocol. One embodiment of computer 142 or 144 is computer 1202 in FIG. 12.

In some embodiments, computer 142 or 144 receives notice from the PMs 134 and 136 of abnormalities in the measurements of the health of the living subject, and consequently instructs the injector system 122 and 124 respectively to halt infusion or take other appropriate corrective action. In still further embodiments, computer 142 or 144 instructs the scanner 138 or 140 to initiate a scanning operation at an appropriate time after infusion by the injector system 122 or 124, respectively. In still further embodiments, one injector system is controlled by its stand-alone user interface and used to inject a prescribed amount of radioactivity in patients who are scanned either sequentially on a single scanner, or in parallel on multiple scanners.

Portions of the PET imagining systems 114 or 116 are known as dosing stations. One dosing station in FIG. 1 includes injector system 122, PM 134 and computer 142. Another dosing station in FIG. 1 includes injector system 124, PM 136 and computer 144.

In some embodiments, system 100 includes a control system 146. The control system 146 is operable to receive status information from, and send commands to, the PET devices such as the cyclotron 101, dispensing station 106, quality control device 110, injector systems 122 and 124, physiologic monitors 130 and 136, scanners 138 and 140, and computers 142 and 144. In some embodiments, a computer program in the control system 146 is operable to calculate amounts of multidose radiotracer 104 to be transported to the injector system 124 based on specific site control variables. One embodiment of computer 146 is computer 1202 in FIG. 12.

In some further embodiments, control variables include the distance and transfer time between the scanner 138 or 140 and a cyclotron 101 that produces nitrogen-13 ammonia. In those embodiments, system 100 provides a convenient method for on-site production and administration of nitrogen-13 ammonia radiopharmaceutical for cardiac studies.

In yet further embodiments, a computer program in the control system 146 stores production and dosing data. Thus system 100 provides for a more centralized storage of records in the preparation, delivery, monitoring and injection of radiotracers to patients, which reduces disjoint management and control of those functions that conventional systems exhibit.

In yet a further embodiment, data that describes high level descriptors of one or more living subjects to be treated by system 100 is read from a PET scanner 138 or 140, or other device. One example of the other devices is a patient information system in the medical facility. The data is received by the control system 146. The high level descriptors include the prescribed dose for each living subject and the injection time schedule for the living subjects. In still further embodiments, the data includes the type of radiopharmaceutical (e.g. oxygen-15), a predefined parametric equation, and/or clinical protocol being followed in the medical procedure.

Based on this data, the required radiotracer dose activity is calculated and compared to the total activity available in the multidose portion of the radiotracer 104. If there will be a shortage, the system 100 will notify the operator. If the cyclotron 101 is managed by an outside radioisotope supplier, the supplier will be notified via an Internet link or other electronic means. The supplier will be notified of the additional dose activity required and what time the additional radiotracers will be required.

System 100 provides scalable economies of efficiency. Economy of scale is provided by the use of more than one PET imaging system for each dispensing station 106, quality control unit 110 and each control system 146.

Figure 12:
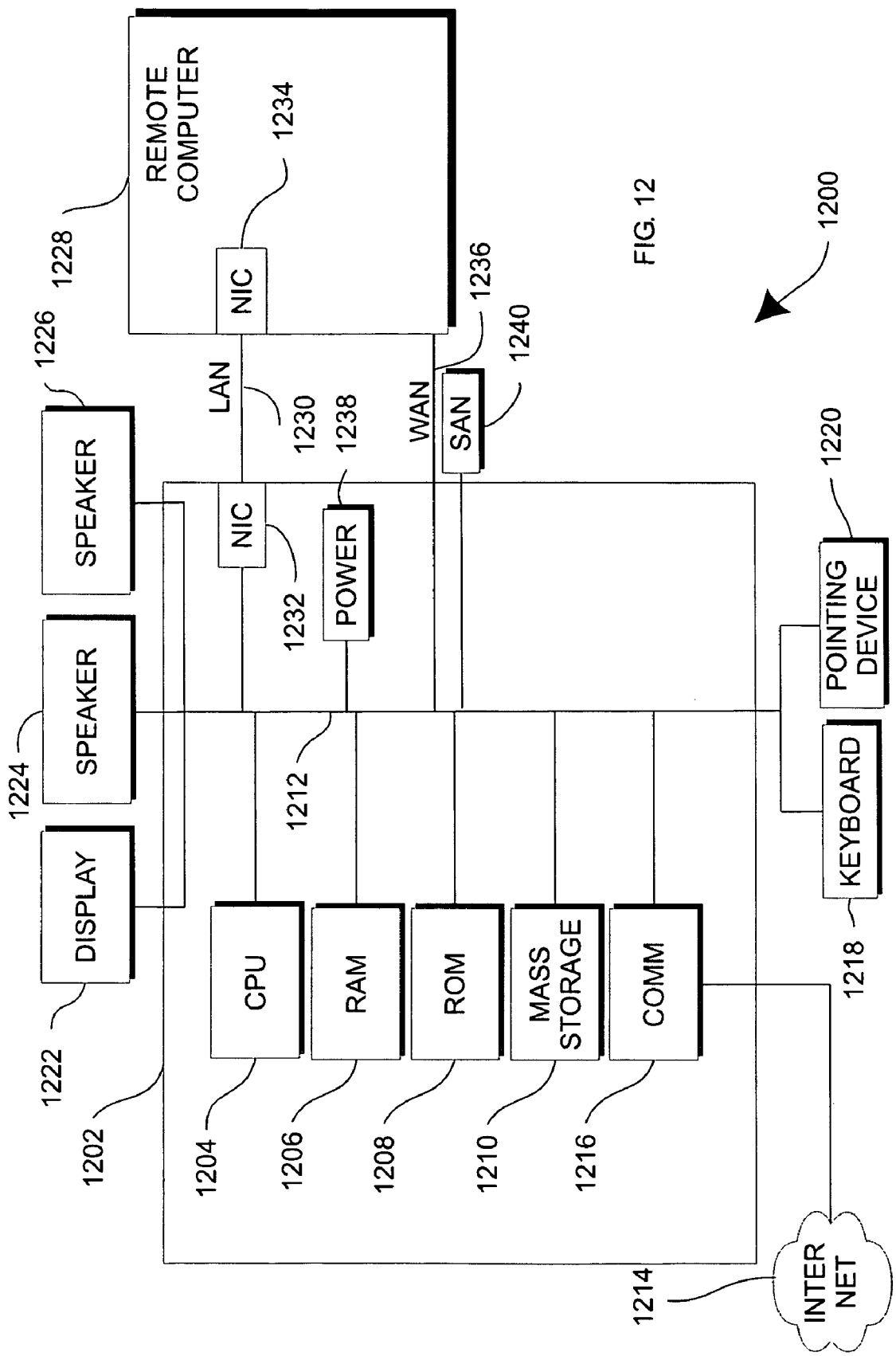
FIG. 12 is a block diagram of the hardware and operating environment in which different embodiments can be practiced.

In some embodiments, control system 146 is a computer system, such as shown in FIG. 12. In some embodiments, the control system 146 is operably coupled to the PET devices through a local area network (LAN) 148. Communication links of the LAN may be implemented either through physical cabling or though a wireless link. Communication links between the LAN 148 and the PET imaging systems 114 and 116 and the cyclotron are implemented through LAN interfaces that are well-known in the art. In some embodiments, the physiologic monitoring devices 134 and 136 are also operably coupled directly to the LAN 148. In embodiments where the cyclotron 101, the devices that are within the radiation shield 112, and/or the scanning systems 114 and 116 are in different facilities, the LAN communication links between these portions of the system are wide-area networks. As an alternative to a LAN 148, the devices of system 100 may be operably coupled through a direct communication link.

In some embodiments, the control system 146 manages the process of producing the radiotracer 104 and delivering the radioisotope according to the current requirements of a PET imaging system. The control system 146 is capable of receiving information describing an amount of a requested individual dose 126 or 128, sending instructions to the cyclotron 101 to produce the individual quantity of the radioisotope, sending instructions to the dispensing station to dispense the individual quantity of the radioisotope to the requesting PET imaging system. In some embodiments, the request is initiated by an operator of the graphical user interface of a computer 142 or 144 in a PET imaging system 114 or 116. In some embodiments, control system 146 receives notice from the PMs 134 and 136 of abnormalities in the measurements of the health of the living subject, and consequently instructs the injector system 122 and 124 respectively, to halt infusion. In yet some further embodiments, when the QC 110 indicates that quality is below acceptable minimum standards, the control system 146 provides notice to an operator of the control system 146 of the indications of the unacceptable quality and instructs the systems to purge the radiotracer from the apparatus.

In still further embodiments, control system 146 instructs the scanner 138 or 140 to initiate a scanning operation at an appropriate time after infusion by the injector system 122 or 124, respectively. In yet further embodiments, scanner 138 or 140 follows a pre-defined set of acquisition strategies depending on a radiotracer and a clinical protocol being use. In some embodiments, the acquisition strategies includes initiation of scanning after a predefined time following injection of the radiotracer, introducing a pharmaceutical stress agent followed by injection of radiotracer and imaging once again after predefined time.

Furthermore, in some embodiments portions of the system 100 are mounted inside a moveable structure with or without wheels in order to provide a portable or relocateable medical radiopharmaceutical administration system 100 for preparation and injection of radiopharmaceuticals from multiple doses of the radiopharmaceutical. In one example, the radiation shield 112 is mounted on a structure having wheels so the portions of the system within the radiation shield that are radioactive are more easily moved from one location to another.

The system level overview of the operation of an embodiment has been described in this section of the detailed description. System 100 is an integrated system for production, quality control distribution and imaging using PET radiopharmaceuticals. System 100 reduces the disjoint management and control of the functions of preparing and injection radioisotopes into living subjects. System 100 provides an end-to-end control system which treats the clinical challenges of administering radioisotopes to living subjects as a single problem, and provides and integrated production, dispensing, quality control, infusion, data acquisition scheme in an automated manner. In addition, it provides an automated way of administering sequential PET imaging protocols such as in rest-stress cardiac PET imaging.

While the system 100 is not limited to any particular cyclotron 101, multidose portion of radiotracer 104, dispensing station 106, individual portion of radiopharmaceutical 126 and 128, PET imaging systems 114 and 116, shield 112, quality control device 110, injector systems 122 and 124, physiologic monitors 134 and 136, scanners 138 and 140, and computers 142 and 144, control system 146 and LAN 148. For sake of clarity, simplified components have been described.

Apparatus of an Embodiment

In the previous section, a system level overview of the operation of an embodiment was described. In this section, the apparatus of such an embodiment are described by reference to a series of block diagrams. Describing the apparatus enables one skilled in the art to make and use the apparatus.

Figure 2:
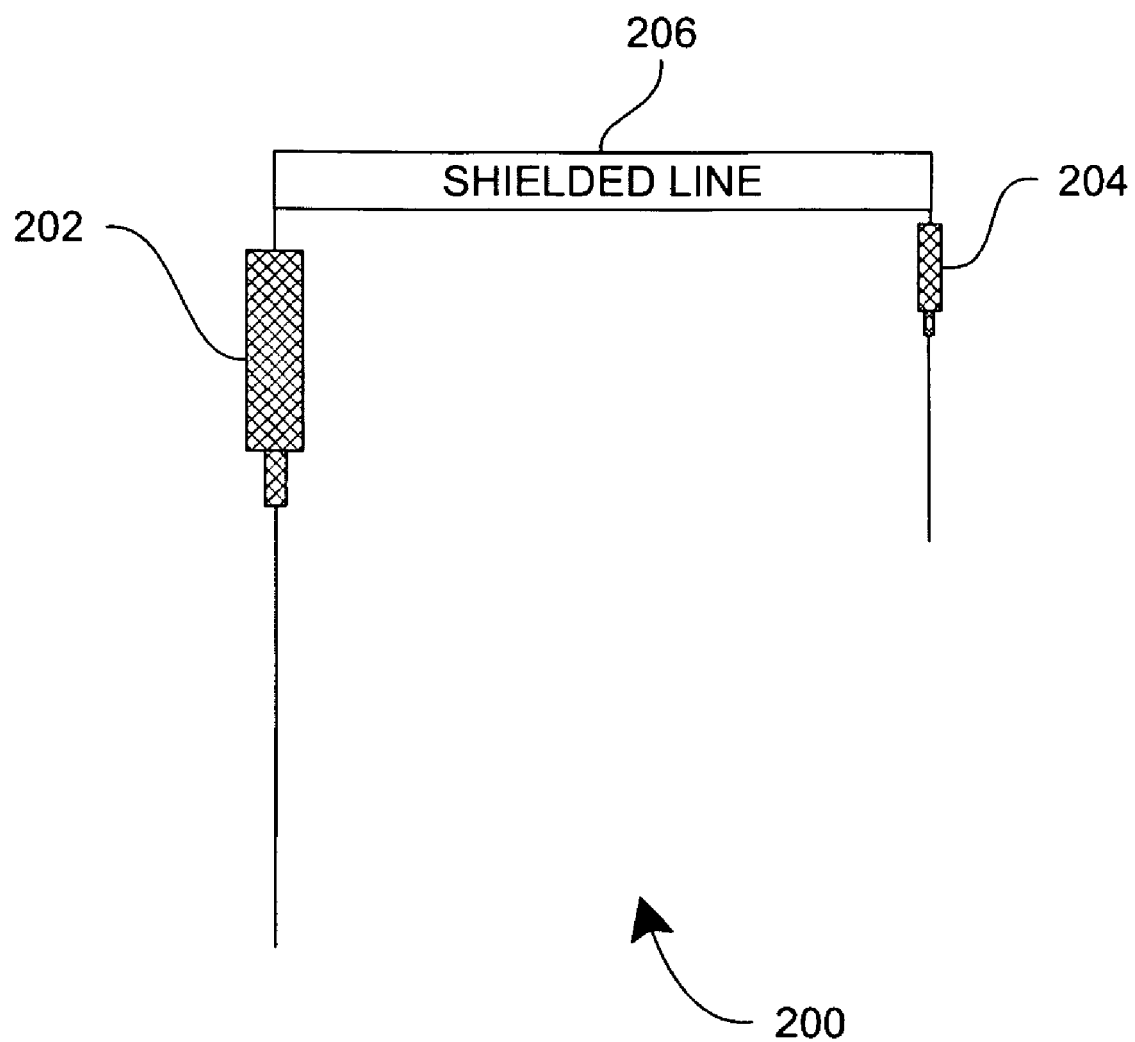
FIG. 2 is a block diagram of an apparatus for injecting one or more individual doses of a radiopharmaceutical from a multiple dose of the radiopharmaceutical.

FIG. 2 is a block diagram of an apparatus 200 for injecting one or more individual doses 126 or 128 of a radiopharmaceutical from a multiple dose of the radiopharmaceutical. Apparatus 200 includes an extraction apparatus 202. The lower end of the extraction apparatus 202 is placed in a multiple dose of the radiopharmaceutical. An individual dose 126 or 128 is removed from the multiple dose of the radiopharmaceutical by the extraction apparatus 202 through a suction or vacuum action. The extraction of an individual dose 126 or 128 of a radiopharmaceutical from a multiple dose of the radiopharmaceutical reduces the number of individual dose vials and shielded containers that radioisotope suppliers prepare and deliver to each medical facility each day. The extraction of an individual dose 126 or 128 also reduces the number of delivery trips that a radiotracer supplier makes to each medical facility each day. FIG. 2 shows one example of an extraction apparatus 202 that is a drug delivery system.

The extraction apparatus 202 is operably coupled to an intravenous injection apparatus 204 having an intravenous needle. The extraction apparatus 202 is coupled through intravenous tubing 206. Tubing provides operable coupling through which liquids can be transferred, transported and/or distributed. In some embodiments, the tubing 206 is a lead-shielded line that reduces the exposure of people, such as PET technicians, to radioactivity during the manual steps of administering a radiopharmaceutical to patients. The individual dose of the radiopharmaceutical is dispensed through the tubing 206 and injected in a living subject through the intravenous injection apparatus 204.

Thus, apparatus 200 allows individual doses 126 or 128 of a radiopharmaceutical to be dispensed from a multiple dose of the radiopharmaceutical and injected in a living subject at the same medical facility. The apparatus 200 also provides a more convenient means of preparing and distributing individual doses 126 or 128 of a radiopharmaceutical than conventional systems that require irradiation and shipment of each individual doses of radiopharmaceutical.

Figure 3:
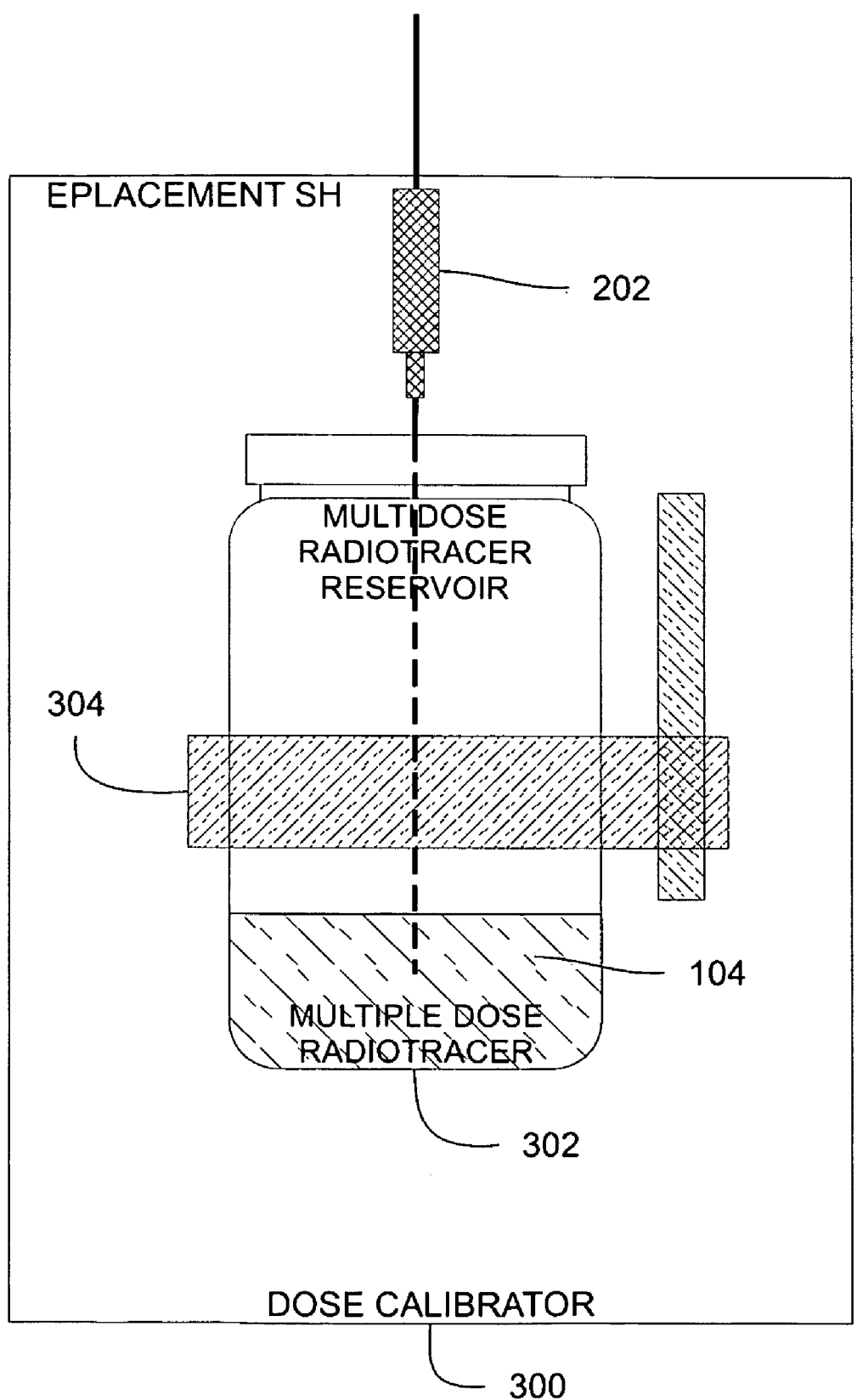
FIG. 3 is a block diagram of a dispensing station according to an embodiment.

FIG. 3 is a block diagram of a dose calibrator system 300 according to an embodiment. The dose calibrator system 300 allows a multidose portion of radiopharmaceutical to be dispensed as one or more individual doses. A multidose portion of a radiopharmaceutical is a quality-controlled quantity of a radiotracer 104 that is reasonably calculated to provide radioactivity for more than one dose of radioactivity. An individual dose of a radiopharmaceutical is a quantity of a radiopharmaceutical that is reasonably calculated to provide radioactivity for one dose of radioactivity.

The dose calibrator system 300 receives a reservoir 302 to contain a multiple dose of a radiopharmaceutical in FIG. 1. The reservoir 302 is received into a cavity of the dose calibrator system 300. The reservoir 302 is also known as a multidose vial. A mechanical holding apparatus 304, such as a carriage arm, holds the reservoir 302 inside the dispensing station. In some embodiments, the mechanical holding apparatus 304 is mounted on the inside of the cavity of the dose calibrator system 300. The multidose vial 302 in system 300 reduces the number of vials of individual doses that a radiotracer supplier needs to deliver to a medical facility each day, which in turn reduces the number of delivery trips that a radiotracer supplier needs to provide to each medical facility each day.

The dose calibrator system 300 extracts individual doses 126 or 128 of radiopharmaceutical from the reservoir 302 through an extraction apparatus 202. The extraction apparatus 202 is mounted to the dose calibrator system 300, such as being mounted inside the cavity of the dose calibrator system 300. The individual dose 126 or 128 of radiopharmaceutical is dispensed to one or more PET imaging systems 112 and 114 in FIG. 1. Thus, the dose calibrator system 300 allows a multidose portion of radiopharmaceutical to be dispensed from the reservoir 302 as one or more individual doses. Dose calibrator system 300 provides a more convenient means of preparing and distributing individual dose 126 or 128 of radiopharmaceutical than conventional systems that require irradiation and shipment of many individual doses of radiopharmaceutical.

Figure 4:
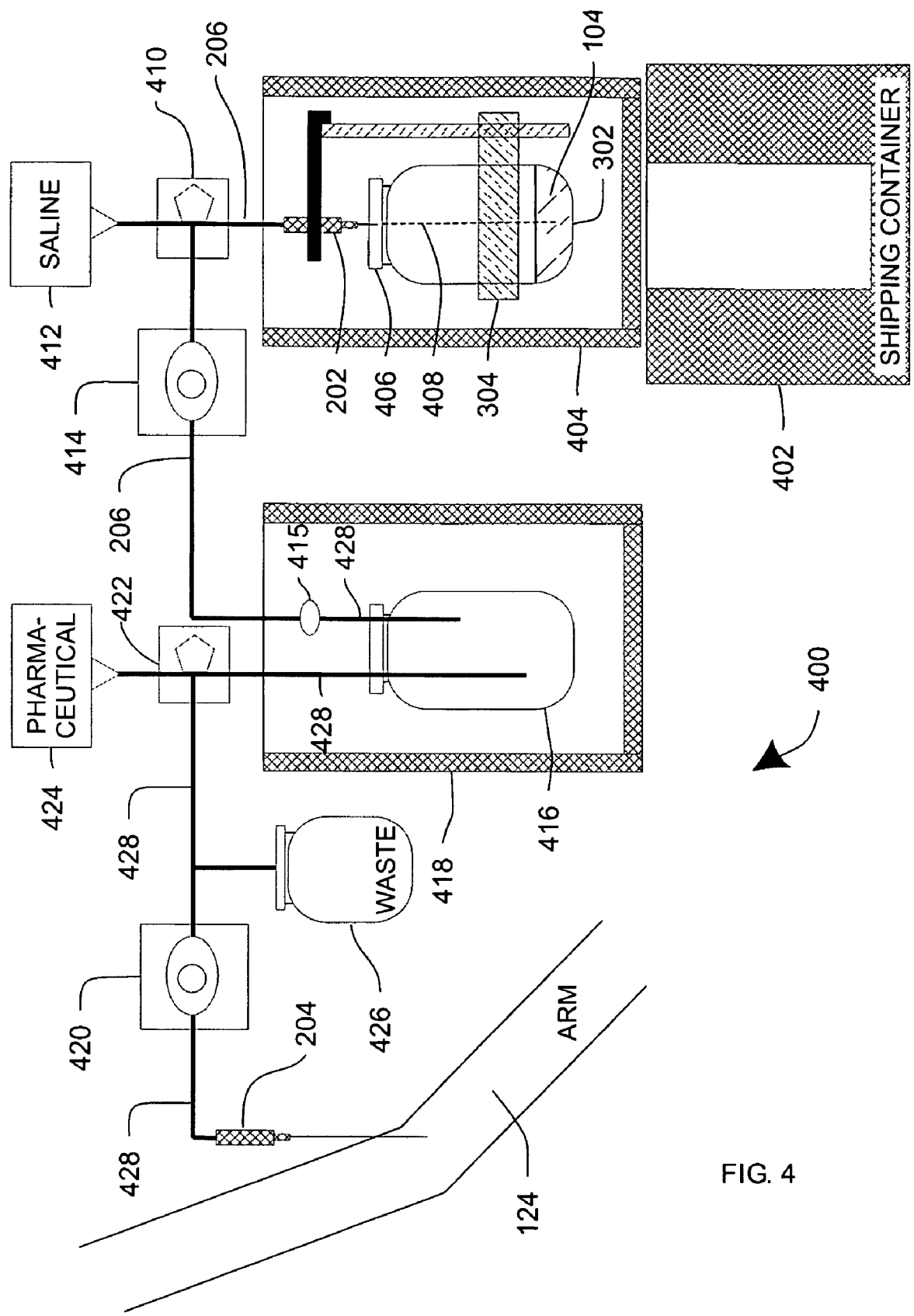
FIG. 4 is a block diagram of an automated injector system for PET medications according to an embodiment.

FIG. 4 is a block diagram of an automated injector system for PET medications 400 according to an embodiment. Injector system 400 is one embodiment of injector systems 122 and 124.

System 400 allows an individual dose of a radiopharmaceutical 126 or 128 to be dispensed from a multidose vial 302. The multidose vial 302 contains a multiple dose portion of a radiotracer. The multidose vial 302 is delivered by a radiotracer supplier to the site of the system 400 in a lead-shielded shipping container 402. The multidose vial 302 in system 400 reduces the number of vials of individual doses that the radiotracer supplier needs to deliver to a medical facility each day, which in turn reduces the number of delivery trips that the radiotracer supplier needs to provide to each medical facility each day.

The shipping container 402 is placed into a fixed position under a lead-shielded dose calibrator system 404 (also known as an ion-chamber) and the top cover 306 of the multidose vial 302 is removed. The top cover 406 may be removed either manually or by automated mechanical means. An example of an automated means is one in which a pneumatic arm 304 lowers into the shipping container 402 and attaches to the multidose vial 302. The multidose vial 302 is raised from the shipping container 402 into the dose calibrator system 404 and a needle 408 is automatically inserted into the multidose vial 302. An individual dose 126 or 128 is extracted from the multiple dose of the radiopharmaceutical by the extraction apparatus 202 through a suction or vacuum action. Thus, system 400 allows a multidose portion of radiopharmaceutical to be dispensed as individual doses 126 or 128. System 400 provides a more convenient means of preparing and injecting an individual dose of a radiopharmaceutical than conventional systems that require irradiation and shipment of many individual doses of radiopharmaceutical. System 400 provides significant economies of scale in the preparation and distribution of doses of radiopharmaceuticals.

The extraction means 302 extracts an amount of radiopharmaceutical that is reasonably calculated to provide an individual dose of the radiopharmaceutical 126 or 128. The amount of the individual dose 126 or 128 is calculated based on the type of radiopharmaceutical, the radioactive half-life of the radiopharmaceutical, a predefined parametric equation, clinical protocol being followed, the projected time of injection into a living subject 124 and high level descriptors of the living subject, such as the weight, sex and physical dimensions of the living subject.

Components of system 400 have predefined sizes and shapes that are designed to physically integrate with each other. In one example, the multidose vial 302 and the shielded shipping container 402 have predefined sizes and shapes that are designed to physically integrate with each other. In another example, the multidose vial 302 and the lead-shielded dose calibrator system 404 have predefined sizes and shapes that are designed to physically integrate with each other. The integrated shapes allow the components to fit together within prescribed tolerances to reduce escape of radioactive materials and to allow automated processes such as the multidose vial 302 being removed by a carriage arm from the shielded shipping container 402 and being received into the dose calibrator system 404. In some embodiments, the predefined sizes and shapes are specified by a radiotracer supplier, and are unique to that radiotracer supplier. Having predefined sizes and shapes of the components provides strong incentive to a medical facility to continue patronage of the radiotracer supplier where the multidose vial 302 and the shielded shipping container 402 may not have a size and shape that is physically compatible with the dose calibrator system 404 to the extent that the dose calibrator system 404 may not receive the multidose vial 302.

In some embodiments, the extraction means 202 is operably coupled through intravenous tubing 206 to a device that regulates the flow of multiple liquids, such as a solenoid driven 3-way stopcock 410 or another type of multiport value. The stopcock 410 is also operably coupled to a reservoir of another liquid pharmaceutical, such as an intravenous bag of sodium chloride (NaCl) of appropriate concentration 412 commonly known as saline. The individual dose 126 or 128 is mixed with the NaCl 412 by the stopcock 410. The mixture is pumped from the stopcock 410 by a pump 414, such as a peristaltic pump.

In some embodiments, a second reservoir 416 in a second dose calibrator 418 receives the mixture from the peristaltic pump 414. In some embodiments, the reservoir 416 is a vial that has a "V" shaped bottom and is known as a patient vial. The mixture passes through a filter 415, such as a 0.22 micron radiotracer filter, and is stored in the second reservoir 416. In some embodiments, an infusion pump is operably coupled to the peristaltic pump 414 as an alternative to the reservoir 416 in a second dose calibrator 418. In some embodiments, the dose calibrator includes an ion chamber that measures the amount of radioactivity of the mixture. The measurement of the radioactivity allows the adequacy of the radioactivity of each individual dose to be verified immediately prior to injection, and in close proximity to the site of injection.

The mixture is pumped toward the living subject by an infusion system 420, such as infusion pump, through a second device that regulates the flow of multiple liquids, such as a second solenoid driven 3-way stopcock 422. The stopcock 422 is also operably coupled to a reservoir of another liquid pharmaceutical, such as an intravenous bag containing a non-radiological pharmaceutical 424 such as pharmacological stress agent. Examples of stress agents used in myocardial perfusion studies include dipyridamole and adenosine. In some embodiments, a receptacle for waste 426 is operably coupled to the intravenous tube 206 between the device that regulates the flow of multiple liquids 422 and the infusion pump 420.

The infusion pump 420 pumps the mixture into the living subject 124 through an intravenous injection apparatus 204 having an intravenous needle, thus providing an individual dose 126 or 128 of a radiopharmaceutical to a living subject 124 from a multiple dose 104 of the radiopharmaceutical. In various embodiments, the radiopharmaceutical is also mixed with other pharmaceuticals such as saline 412 and/or a pharmaceutical 424, thus providing flexibility in configurations to support a variety of medical applications.

In some embodiments of system 400, a dose meter verifies the quantity of the individual dose 126 or 128 of the radiopharmaceutical. The dose meter may be operably coupled to either the intravenous tubing 206 or intravenous tubing 428. IV tubing is also known as patient tubing. In other embodiments, system 400 also includes one or more additional dose calibrators 404. The additional dose calibrator(s) 404 allow the system to inject radiopharmaceutical(s) other than the radiopharmaceutical in dose calibrator system 404.

In order to protect living subjects from exposure to pharmaceuticals and microorganisms of living subjects who have used the system 400 earlier, numerous components of the system are replaced for each use. The components that are replaced after each use of the system are all of the disposable items situated between the filter 415 and the living subject 124. The disposable items include the IV tubing 428 and intravenous injection apparatus 204.

Figure 8:
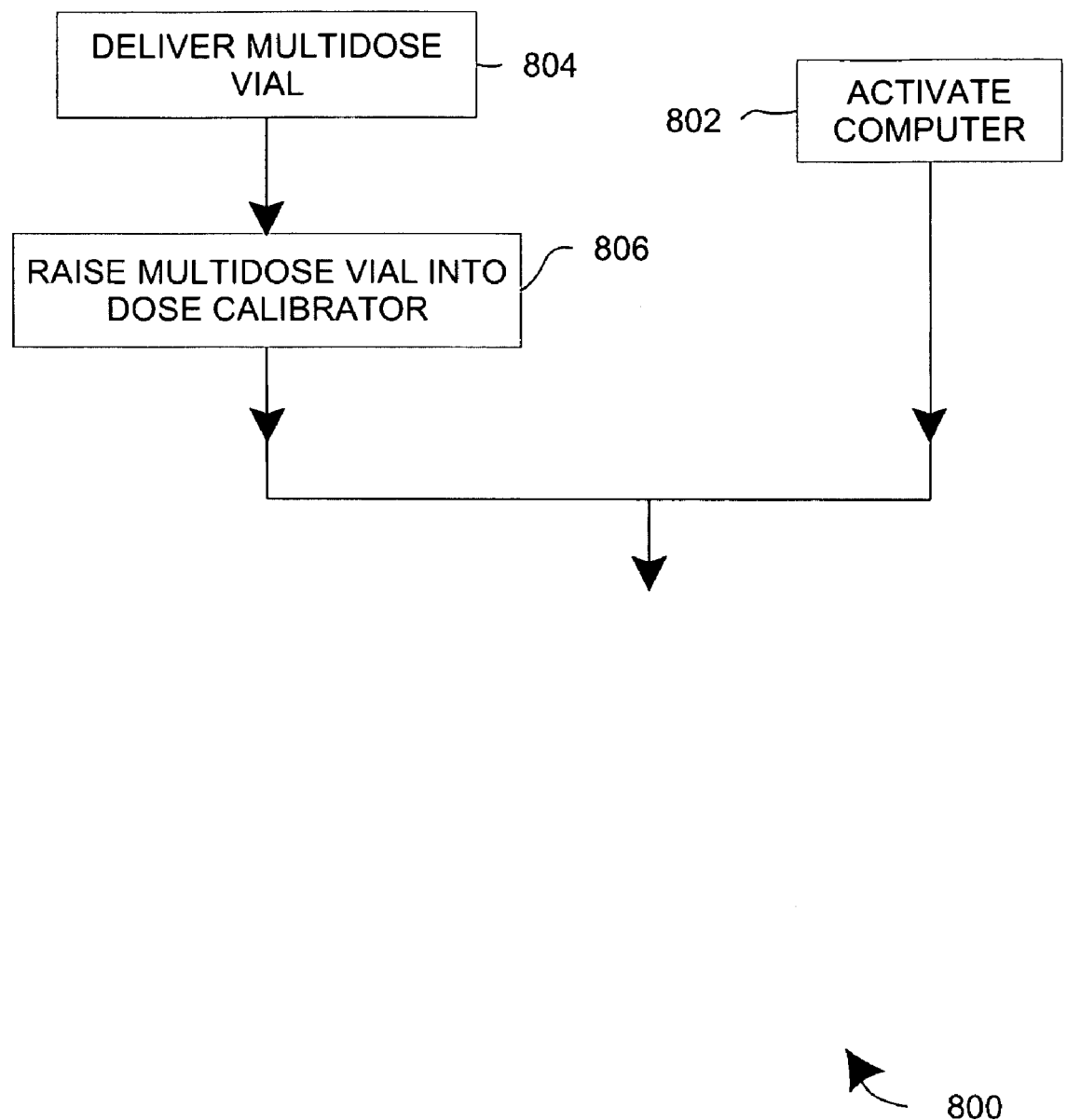
FIG. 8 is a flowchart of an embodiment of a method of preparing an injector system for use by a number of patients.

One example of the operation of system 400 is described in detail in method 800 in FIG. 8.

Figure 5:
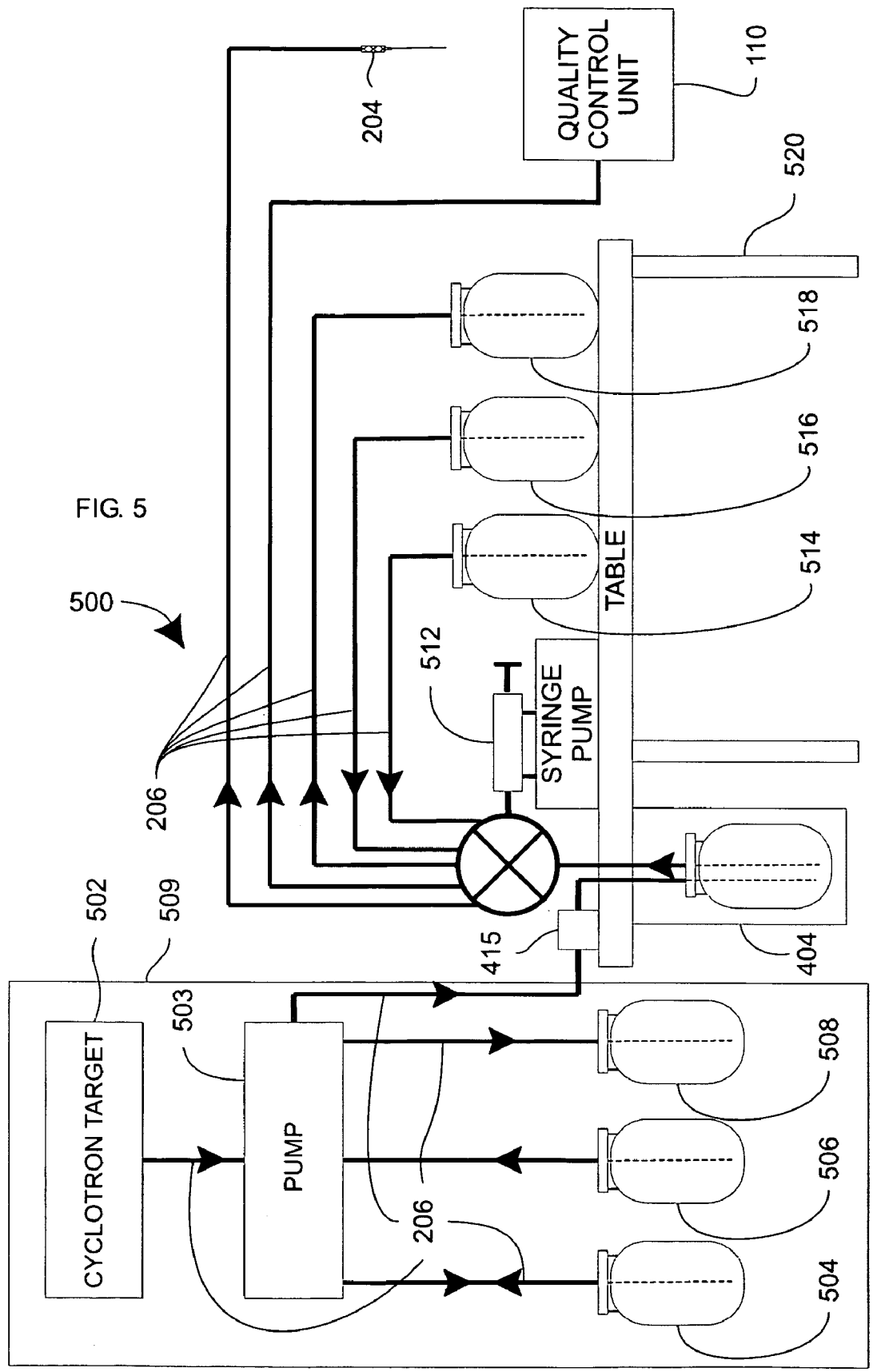
FIG. 5 is a block diagram of a medical radiopharmaceutical administration system according to an embodiment.

FIG. 5 is a block diagram of a medical radiopharmaceutical administration system according to an embodiment 500. The medical radiopharmaceutical administration system 500 is an integrated system for production, quality control and injection of individual doses of a radiopharmaceutical in positron emission tomography (PET) imaging.

In system 500, a cyclotron target 502 produces a radioisotope, such as nitrogen-13 ammonia. In the nitrogen-13 ammonia embodiments, the target material that is placed in the cyclotron target 502 may be either an ethyl alcohol mixture of appropriate molarity in high resistivity water, methane over pressure on water, or simply water followed by reduction of anions using DeVarda's alloy. Furthermore, the cyclotron target 502 has a cavity volume of between about 0.5 milliliters and less than about 10 milliliters.

A pump 503 receives the radioisotope and deposits the radioisotope in a holding reservoir 504. The radioisotope is circulated within the holding reservoir 504.

Later, the pump receives the radioisotope from the holding reservoir 504. The pump also receives optionally, a rinse solution 506. The pump 503 also returns waste to reservoir 508. Waste is additional unneeded portions of the radioisotope and/or the rinse solution 506.

Components of the system 500 that produce the radioisotope mixture, such as pump 503, the cyclotron target 502, the radioisotope reservoir 504, the rinse solution 506, and the waste reservoir 508 are all located in the same room 509 with a cyclotron. The remainder of the components of system 500 may be located in the same building as the cyclotron room 509, or in a nearby building in the same medical complex.

In some embodiments, the mixture of the nitrogen-13 ammonia or other radioisotope and the rinse solution 506 flows from the pump 503 into a filter 415, such as a 0.22 micron radiotracer filter.

The mixture flows into a dose calibrator system 404. The dose calibrator system 404 extracts an individual dose 126 or 128 of the mixture. The individual dose flows into an infusion device such as syringe pump 512 or an infusion pump. In some embodiments, sterile water for injection from reservoir 514 and/or a stress agent from a stress agent reservoir 516 also flows into the syringe pump 512. The water is used as a flush for the lines 206. From the syringe pump, the mixture of the individual dose, the water and the stress agent flows into an intravenous injection apparatus 204 having an intravenous needle, through intravenous tubing, injection into a living subject. Thus dose calibrator system 404 allows a multiple dose of a radiopharmaceutical to be administered to one or more living subjects in individual doses, optionally with a stress agent, sterile water, and a rinse solution. The dose calibrator system 404 reduces the number of vials of individual doses that a radiotracer supplier needs to deliver to a medical facility each day, which in turn reduces the number of delivery trips that a radiotracer supplier needs to provide to each medical facility each day.

Waste from the syringe pump 512 also flows to a waste reservoir 518. The quality of the mixture of dose is monitored by the quality control unit 110. Intravenous tubing 206 is used in system 500 to transport the liquids and mixtures.

Portions or all of the system 500 may be placed on a table 520 or mounted on a support structure. Furthermore, portions of the system 500 may also be mounted inside a moveable structure having wheels in order to provide a portable medical radiopharmaceutical administration system 500 for preparation and injection of individual doses of a radiopharmaceutical from multiple doses of the radiopharmaceutical.

System 500 provides a convenient method for on-site production and administration of radiotracer, such as nitrogen-13 ammonia.

Figure 6:
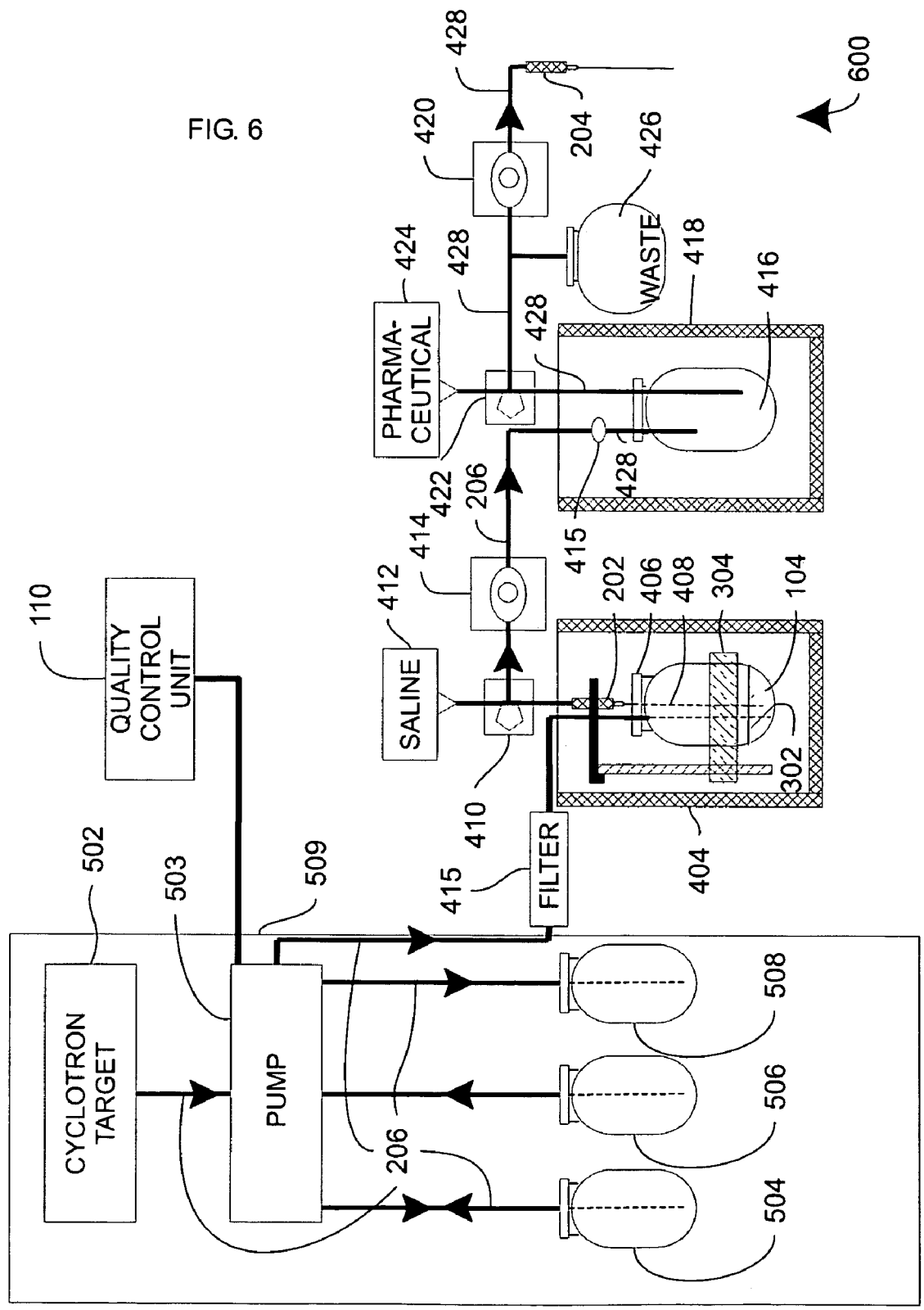
FIG. 6 is a block diagram of a medical radiopharmaceutical administration system according to an embodiment.

FIG. 6 is a block diagram of a medical radiopharmaceutical administration system according to an embodiment 600. The medical radiopharmaceutical administration system 600 is an integrated system for production, quality control and injection of individual doses of a radiopharmaceutical in positron emission tomography (PET) imaging.

In system 600, a cyclotron target 502 produces a radioisotope, such as nitrogen-13 ammonia. In the nitrogen-13 ammonia embodiments, the target material that is placed in the cyclotron target 502 to produce nitrogen-13 ammonia may be either an ethyl alcohol mixture of appropriate molarity in high resistivity water, methane over pressure on water, or simply water followed by reduction of anions using DeVarda's alloy. Furthermore, the cyclotron target 502 has a cavity volume of between about 0.5 milliliters and less than about 10 milliliters.

A pump 503 receives the radioisotope and deposits the radioisotope in a holding reservoir 504. The radioisotope is circulated within the holding reservoir 504.

Later, the pump receives the radioisotope from the holding reservoir 504. The pump also receives optionally, a rinse solution 506. The pump 503 also returns waste to reservoir 508. Waste is additional unneeded portions of the radioisotope and/or the rinse solution 506.

In some embodiments, the mixture of the radioisotope and the rinse solution 506 flows from the pump 503 into a filter 415, such as a 0.22 micro radiotracer filter. The quality of the mixture is tested by quality control unit 110.

The mixture flows into a dose calibrator system 404. The dose calibrator system 404 extracts an individual dose 126 or 128 of the mixture through extraction apparatus 202 by a suction or vacuum action. Thus, system 600 allows a multidose portion of radiopharmaceutical to be dispensed as individual doses 126 or 128. System 600 provides a more convenient means of preparing and injecting an individual dose of a radiopharmaceutical than conventional systems that require irradiation and shipment of many individual doses of radiopharmaceutical. System 600 provides significant economies of scale in the preparation and distribution of doses of radiopharmaceuticals. The multidose vial 302 in system 600 reduces the number of vials of individual doses that a radiotracer supplier needs to deliver to a medical facility each day, which in turn reduces the number of delivery trips that a radiotracer supplier needs to provide to each medical facility each day.

The extraction means 302 extracts an amount of radiopharmaceutical that is reasonably calculated to provide an individual dose of the radiopharmaceutical 126 or 128. The amount of the individual dose 126 or 128 is calculated based on the radioactive half-life of the radiopharmaceutical, the projected time of injection into a living subject 124 and the weight of the living subject 124.

In some embodiments, the extraction means 202 is operably coupled through intravenous tubing 206 to a device that regulates the flow of multiple liquids, such as a solenoid driven 3-way stopcock 410 or another type of multiport value. The stopcock 410 is also operably coupled to a reservoir of another liquid pharmaceutical, such as an intravenous bag of sodium chloride (NaCl) 412 commonly known as saline. The individual dose 126 or 128 is mixed with the NaCl 412 by the stopcock 410. The mixture is pumped from the stopcock 410 by a peristaltic pump 414.

In some embodiments, a second reservoir 416 in a second dose calibrator 418 receives the mixture from the peristaltic pump 414. The mixture is stored in the second reservoir 416. In some embodiments, an infusion pump is operably coupled to the peristaltic pump 414 as an alternative to the reservoir 416 in a second dose calibrator 418.

The mixture is pumped toward the living subject by an infusion pump 420, through a second device that regulates the flow of multiple liquids, such as a second solenoid driven 3-way stopcock 422. The stopcock 422 is also operably coupled to a reservoir of another liquid pharmaceutical, such as an intravenous bag containing a pharmaceutical 424. In some embodiments, a receptacle for waste 426 is operably coupled to the intravenous tube 206 between the device that regulates the flow of multiple liquids 422 and the infusion pump 420.

The infusion pump 420 pumps the mixture into the living subject 124 through an intravenous injection apparatus 204 having an intravenous needle, thus providing an individual dose 126 or 128 of a radiopharmaceutical to a living subject 124 from a multiple dose 104 of the radiopharmaceutical. In various embodiments, the radiopharmaceutical is also mixed with other pharmaceuticals such as NaCl 412 and/or a pharmaceutical 424, thus providing the flexibility in configurations to support a variety of medical applications.

Methods of an Embodiment

In the previous sections, a system level overview of the operation of an embodiment was described and embodiments of apparatus were described. In this section, the particular methods performed by PET technologists and the control system 146 of such an embodiment are described by reference to a series of flowcharts. Describing the methods by reference to a flowchart enables one skilled in the art to develop manual procedures or computer instructions.

Figure 7:
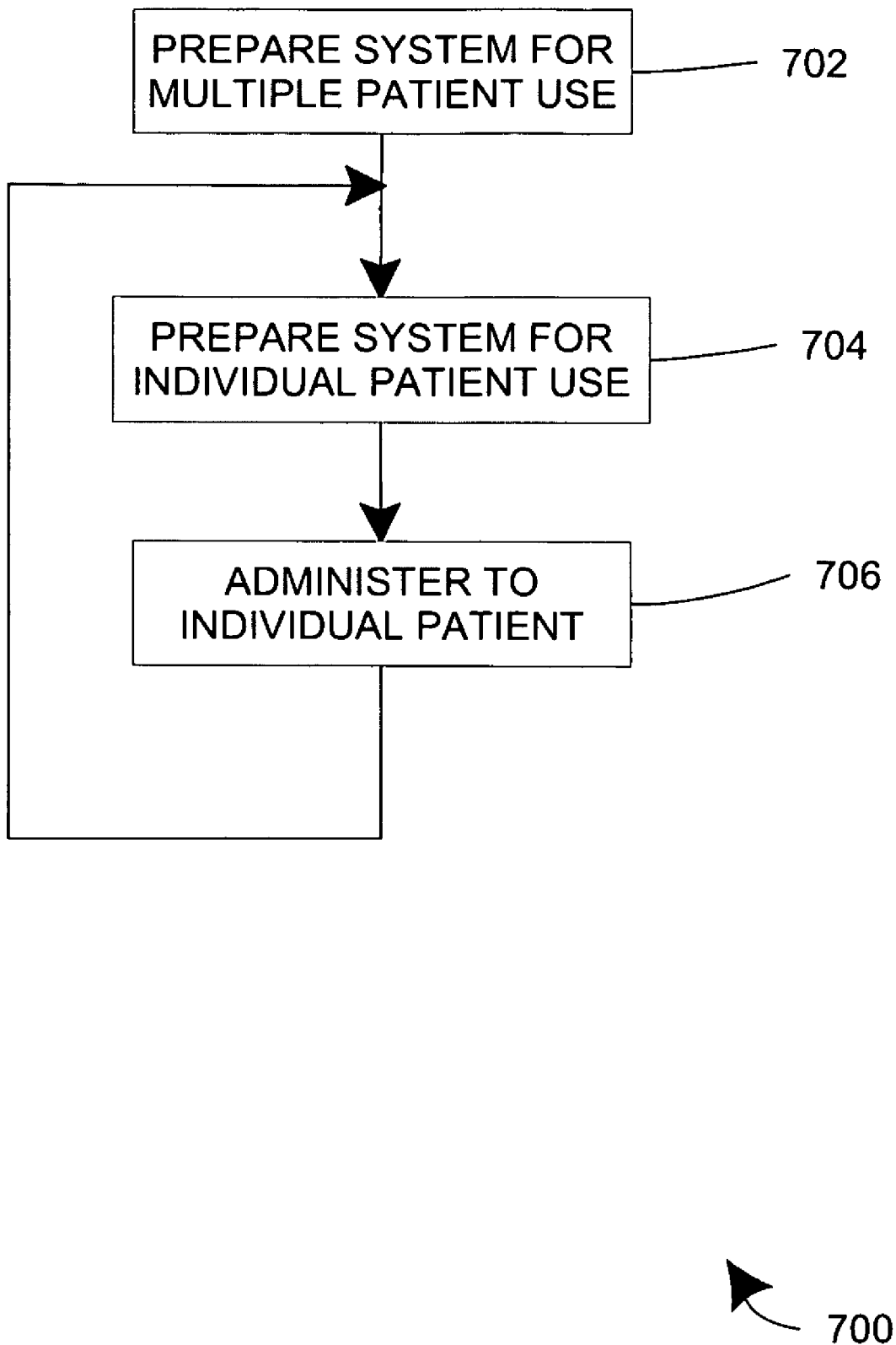
FIG. 7 is a flowchart is an embodiment of a method of operation of an embodiment of the injector system.

FIG. 7 is a flowchart is an embodiment of a method 700 of operation of apparatus 400. Method 700 is performed by a PET technologist. Typically, method 700 is performed once for each day of operation of a PET scanning system.

A PET technologist prepares system 400 for use by a number of patients in action 702, which is described in greater detail in FIG. 8. Then system 400 is repeatedly prepared 704 for each individual patent as described in FIG. 9 and the injection for each patient is administered 706 as described in FIG. 10.

Thereafter, in some embodiments, a radiotracer supplier of the radiopharmaceutical is notified of the number of doses and total activity used for the day and the requirements for the next day.

FIG. 8 is a flowchart of an embodiment of a method 800 of preparing injector system 400 for use by a number of patients. Method 800 is one embodiment of action 702 in FIG. 7.

According to method 800, the computer system 142 or 142 is activated 802.

Method 800 also includes delivering 804 a multidose vial 302 of radioisotope to the system 400. The multidose vial 302 is raised 806 into the dose calibrator system 404.

Figure 9:
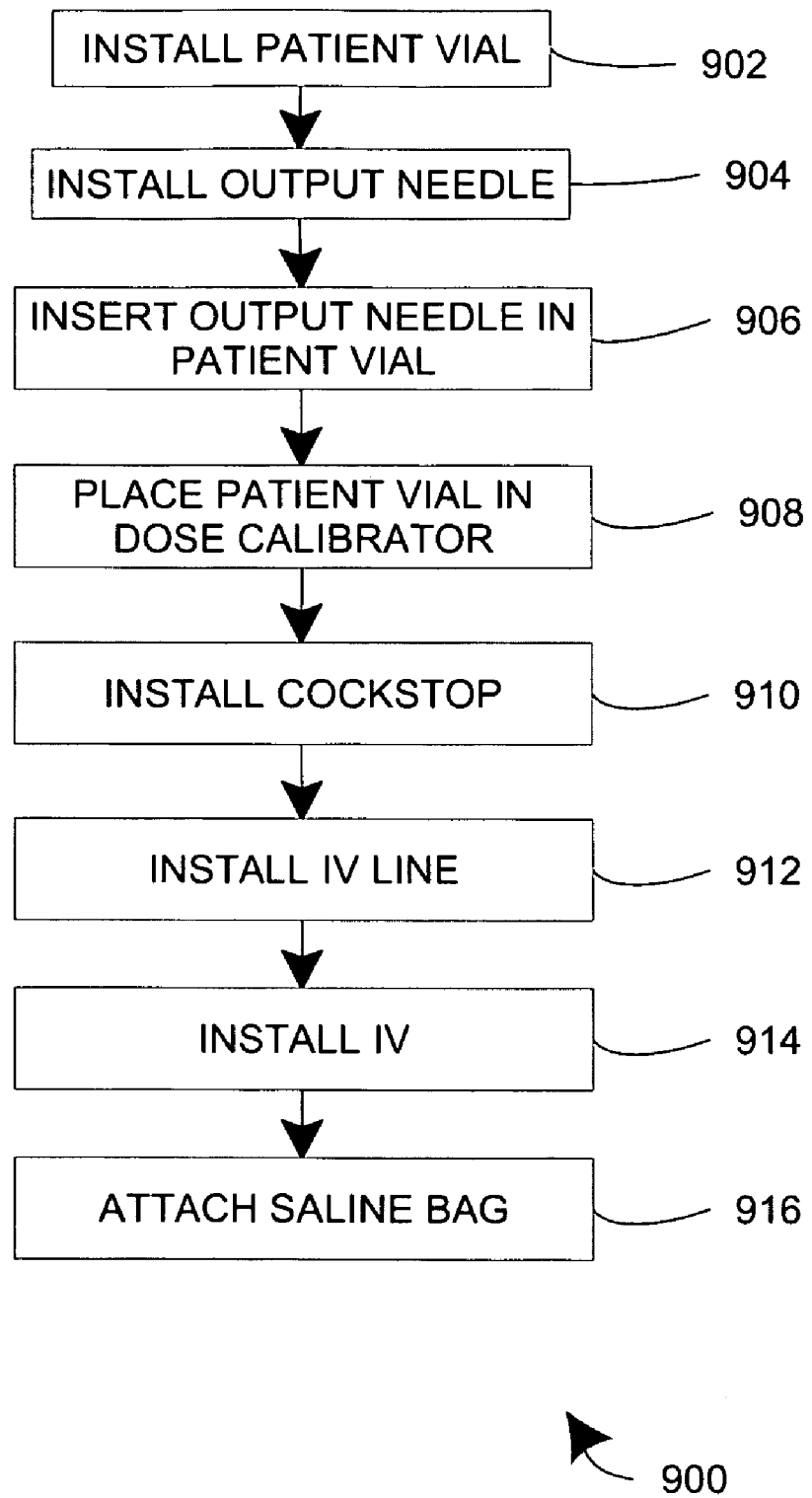
FIG. 9 is a flowchart of an embodiment of method of preparing an injector system for each individual patient.

FIG. 9 is a flowchart of an embodiment of method 900 of preparing an injector system 400 for each individual patient. Method 900 is one embodiment of action 704 in FIG. 7. The actions in method 900 are directed toward installing new disposable items.

Method 900 includes installing 902 a patient vial 416 that is clean, sterile and pyrogens-free into dose calibrator 418. Method 900 also includes connecting 904 an output needle to line 206 from the peristaltic pump 414. The output needle is inserted in 906 or placed at the bottom of the vial 416. Thereafter, the PET technologist places 908 the vial 416 into dose calibrator 418.

Method 900 also includes installing 910 a new stopcock 422. A new IV line 428 is also installed 912 through the new stopcock 422 by feeding the IV line 428 into a first input of 3-way stopcock 410. A new IV 204 is also installed 914. An IV line from a saline bag or a bag of another pharmaceutical 412 is attached 916 to a second input of the 3-way stopcock 410.

Thus, in method 900, a new vial 416, IV line 428, stopcock 422 and IV 204 is used for each patient.

Thereafter, system 400 is ready to begin administration of an individual dose to a patient.

Figure 10:
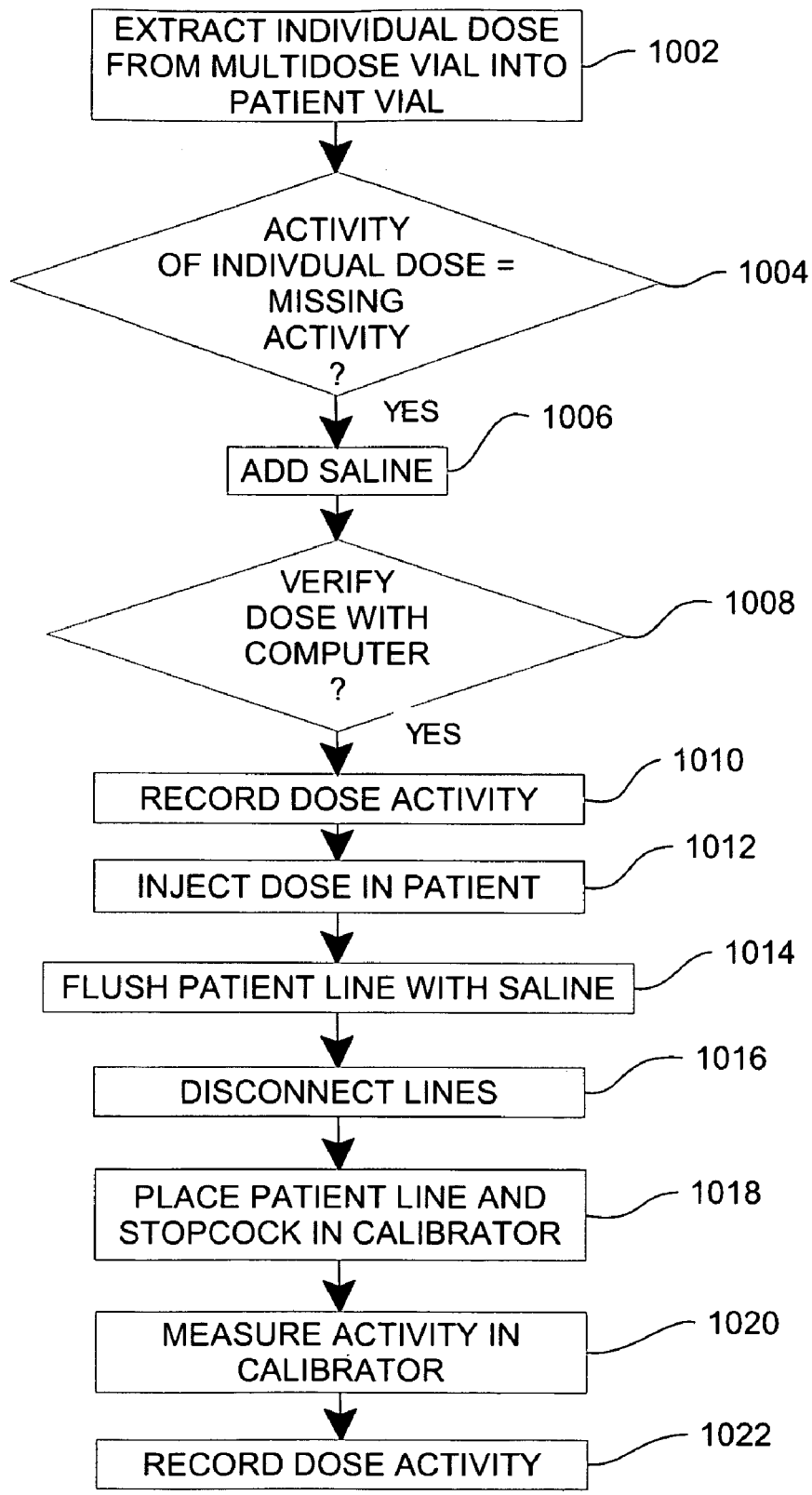
FIG. 10 is a flowchart of an embodiment of a method of administering an injection using injector system in FIG. 4 for each individual patient.

FIG. 10 is a flowchart of an embodiment of a method 1000 of administering an injection using injector system 400 for each individual patient. Method 1000 is an embodiment of action 706 in FIG. 7.

Method 1000 includes extracting 1002 an individual dose of a radiopharmaceutical from a multi dose vial 302. The radiopharmaceutical is pumped through a 3-way stopcock 410 into a patient vial 416 that is located in a patient dose calibrator 418.

When the required amount of radioactivity is present in the patient vial 416, a comparison is done to verify 1004 that the amount of radioactivity in the patient vial 416 is the same amount of radioactivity that has been vacated from the multi dose vial 302. If so, additional saline is added 1006 via the 3-way stopcock 410 and saline bag 412 into the patient vial 416.

The patient dose is recorded by the system 142 or 144 and the recorded dose that is recorded on the computer systems is verified 1008 with the patient vial by the PET technologist. The patient initial dose activity at an initial time is recorded 1010.

The patient is then injected 1012 at a prescribed rate. Note that where the radiotracer is FDG, the injection is performed in a separate room approximately one hour before scanning.

When the activity vial is empty, the patient 3-way stopcock 422 input is selected to saline to allow the flow to flush or purge 1014 the patient line 428 of radioactive substances. After a prescribed time, the saline drip is complete, and the patient line 428 is removed, the stopcock 422 and the saline line are disconnected 1016.

The saline line, patient line 428 and stopcock 422 are placed 1018 into the patient dose calibrator 418 and the residual activity in the patient dose calibrator 418 at this final time is measured 1020. Both the initial dose and residual activities and associated time marks are transmitted 1022 to the PET scanner by the injector system 400.

Describing the following method by reference to a flowchart enables one skilled in the art to develop computer programs, firmware, or hardware, including such instructions to carry out the methods on suitable computerized clients and/or servers executing the instructions from computer-readable media. Similarly, the methods performed by computer programs, firmware, or hardware are also composed of computer-executable instructions.

Figure 11:
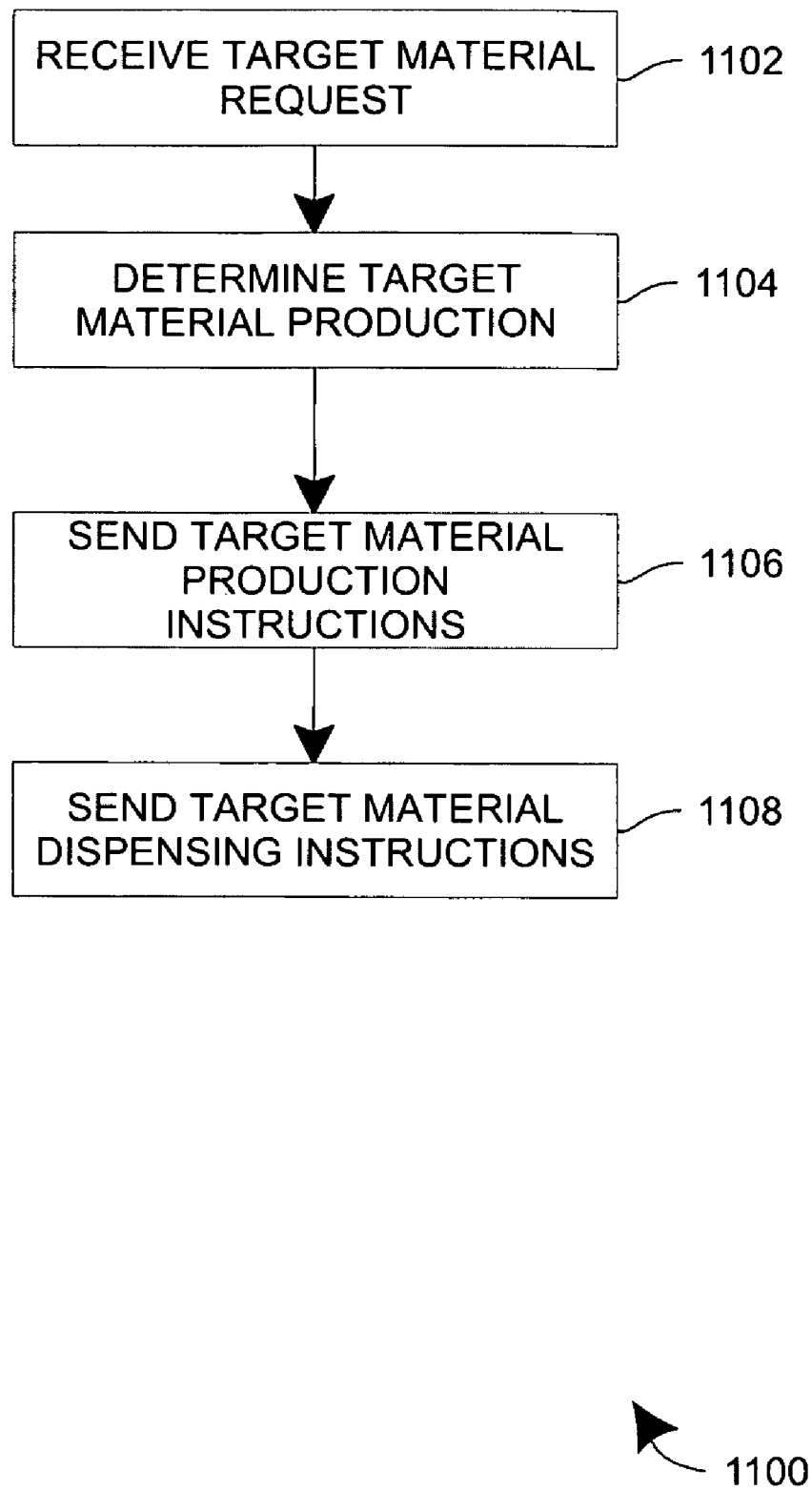
FIG. 11 is a flowchart of a method performed by a control system according to an embodiment.

FIG. 11 is a flowchart of a method 1100 performed by the control system 146 according to an embodiment. The method is directed towards managing radioisotope material in system 1100. Method 1100 is performed by a program executing on, or performed by firmware or hardware that is a part of, a computer, such as computer 1202 in FIG. 12.

Method 1100 includes receiving 1102 information describing a requested amount of radioactivity, the type of radioisotope, the projected time of injection of the radioisotope, high level patient descriptors, and the identification of the PET imaging system that initiated the request. Thereafter, the method includes determining 1104 an amount of target material to be used during the irradiation process, and an amount of radioactivity of the radioisotope to be produced during irradiation. The determining 1104 is calculated from the descriptive information. Thereafter, the method includes sending 1106 instructions to a target in the cyclotron 101 to produce the required quantity of the radioisotope. Subsequently, the method includes sending 1108 instructions to dispensing station 106 to dispense the quantity of the radioisotope to the requesting PET imaging system. Method 1100 reduces the disjoint management and control of the functions of preparing and injecting radioisotopes into living subjects by managing radioisotopes by the control system 146. A technical effect of method 1100 is that the preparation and injection of radioisotopes into living subjects is managed and controlled by computer implemented processes.

In some embodiments, method 1100 is implemented as a computer data signal embodied in a carrier wave, that represents a sequence of instructions which, when executed by a processor, such as processor 1204 in FIG. 12, cause the processor to perform the respective method. In other embodiments, method 1100 is implemented as a computer-accessible medium having executable instructions capable of directing a processor, such as processor 1204 in FIG. 12, to perform the respective method. In varying embodiments, the medium is a magnetic medium, an electronic medium, or an optical medium.

Method 1100 can be embodied as computer hardware circuitry or as a computer-readable program, or a combination of both. In another embodiment, method 1100 is implemented in an application service provider (ASP) system.

More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or inter-process communication techniques such as remote procedure call (RPC), common object request broker architecture (CORBA), Component Object Model (COM), Distributed Component Object Model (DCOM), Distributed System Object Model (DSOM) and Remote Method Invocation (RMI).

Hardware and Operating Environment

FIG. 12 is a block diagram of the hardware and operating environment 1200 in which different embodiments can be practiced. The description of FIG. 12 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 1202 includes a processor 1204, commercially available from Intel, Motorola, Cyrix and others. Computer 1202 is one embodiment of computer 142, 144 or 146 in FIG. 1.

Computer 1202 also includes random-access memory (RAM) 1206, read-only memory (ROM) 1208, and one or more mass storage devices 1210, and a system bus 1212, that operatively couples various system components to the processing unit 1204. The memory 1206, 1208, and mass storage devices, 1210, are types of computer-accessible media. Mass storage devices 1210 are more specifically types of nonvolatile computer-accessible media and can include one or more hard disk drives, floppy disk drives, optical disk drives, and tape cartridge drives. The processor 1204 executes computer programs stored on the computer-accessible media.

Computer 1202 can be communicatively connected to the Internet 1214 via a communication device 1216. Internet 1214 connectivity is well known within the art. In one embodiment, a communication device 1216 is a modem that responds to communication drivers to connect to the Internet via what is known in the art as a "dial-up connection." In another embodiment, a communication device 1216 is an Ethernet® or similar hardware network card connected to a local-area network (LAN) that itself is connected to the Internet via what is known in the art as a "direct connection" (e.g., T1 line, etc.).

A user enters commands and information into the computer 1202 through input devices such as a keyboard 1218 or a pointing device 1220. The keyboard 1218 permits entry of textual information into computer 1202, as known within the art, and embodiments are not limited to any particular type of keyboard. Pointing device 1220 permits the control of the screen pointer provided by a graphical user interface (GUI) of operating systems such as versions of Microsoft Windows®. Embodiments are not limited to any particular pointing device 1220. Such pointing devices include mice, touch pads, trackballs, remote controls and point sticks. Other input devices (not shown) can include a microphone, joystick, game pad, satellite dish, scanner, or the like.

In some embodiments, computer 1202 is operatively coupled to a display device 1222. Display device 1222 is connected to the system bus 1212. Display device 1222 permits the display of information, including computer, video and other information, for viewing by a user of the computer. Embodiments are not limited to any particular display device 1222. Such display devices include cathode ray tube (CRT) displays (monitors), as well as flat panel displays such as liquid crystal displays (LCD's). In addition to a monitor, computers typically include other peripheral input/output devices such as printers (not shown). Speakers 1224 and 1226 provide audio output of signals. Speakers 1224 and 1226 are also connected to the system bus 1212.

Computer 1202 also includes an operating system (not shown) that is stored on the computer-accessible media RAM 1206, ROM 1208, and mass storage device 1210, and is and executed by the processor 1204. Examples of operating systems include Microsoft Windows®, Apple MacOS®, Linux®, UNIX®. Examples are not limited to any particular operating system, however, and the construction and use of such operating systems are well known within the art.

Embodiments of computer 1202 are not limited to any type of computer 1202. In varying embodiments, computer 1202 comprises a PC-compatible computer, a MacOS®-compatible computer, a Linux®-compatible computer, or a UNIX®-compatible computer. The construction and operation of such computers are well known within the art.

Computer 1202 can be operated using at least one operating system to provide a graphical user interface (GUI) including a user-controllable pointer. Computer 1202 can have at least one web browser application program executing within at least one operating system, to permit users of computer 1202 to access intranet or Internet world-wide-web pages as addressed by Universal Resource Locator (URL) addresses. Examples of browser application programs include Netscape Navigator® and Microsoft Internet Explorer®.

The computer 1202 can operate in a networked environment using logical connections to one or more remote computers, such as remote computer 1228. These logical connections are achieved by a communication device coupled to, or a part of, the computer 1202. Embodiments are not limited to a particular type of communications device. The remote computer 1228 can be another computer, a server, a router, a network PC, a client, a peer device or other common network node. The logical connections depicted in FIG. 12 include a local-area network (LAN) 1230 and a wide-area network (WAN) 1232. Such networking environments are commonplace in offices, enterprise-wide computer networks, intranets and the Internet.

When used in a LAN-networking environment, the computer 1202 and remote computer 1228 are connected to a local network 1230 through network interfaces or adapter 1232, which is one type of communications device 1216. Remote computer 1228 also includes a network device 1234. When used in a conventional WAN-networking environment, the computer 1202 and remote computer 1228 communicate with a WAN 1236 through modems (not shown). The modem, which can be internal or external, is connected to the system bus 1212. In a networked environment, program modules depicted relative to the computer 1202, or portions thereof, can be stored in the remote computer 1228.

Computer 1202 also includes a power supply 1238. The power supply can be a battery. In some embodiments, computer 1202 is also operably coupled to a storage area network device (SAN) 1240 which is a high-speed network that connects multiple storage devices so that the multiple storage devices may be accessed on all servers in a LAN such as LAN 1230 or a WAN such as WAN 1236.

Embodiments of 1200 operate in a multi-processing, multi-threaded operating environment on a computer.

CONCLUSION

A radiopharmaceutical distribution system has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, one of ordinary skill in the art will appreciate that implementations can be made in a procedural or objected-oriented design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

The terminology used in this application is meant to include all medical, object-oriented, database and communication environments and alternate technologies which provide the same functionality as described herein.

We claim:

1. A portable medical radiopharmaceutical administration system comprising:
a moveable structure mounted on wheels to be moveable in a medical facility to and from an imaging system, the moveable structure including radioactivity shielding;
a multi-dose container to hold a multi-dose quantity of liquid radiopharmaceutical;
a dispensing station to receive the multi-dose container, the dispensing station having a pump system and a liquid transfer path that is in fluid communication with the multi-dose quantity;
an ion chamber to measure radioactivity, the ion chamber having an ion chamber inlet and an ion chamber outlet, the liquid transfer path entering ion chamber at the ion chamber inlet, the liquid transfer path exiting the ion chamber at the ion chamber outlet;
wherein the multi-dose container, the dispensing station, and the ion chamber are enclosed within the radioactivity shielding while moved on the moveable structure to and from the imaging system; and
a computer system provided on the moveable structure and operably coupled to the pump system and the ion chamber, the pump system to withdraw an individual dose from the multi-dose container and move the individual dose along the liquid transfer path through the ion chamber inlet to the ion chamber, the ion chamber to measure a radioactivity of the individual dose in the ion chamber, the pump system to move the individual dose out of the ion chamber outlet along the liquid transfer path for injection to a patient.

2. The apparatus of claim 1, further comprising:
a local area network operably coupled to at least one positron emission tomography imaging system,
the computer system operably coupled to the local area network to communicate with the at least one positron emission tomography imaging systems.

3. The apparatus of claim 2, further comprising a quality control unit to monitor the radionuclic and chemical purity of the radiotracer that is dispensed by the dispensing station, the quality control unit conveying radiotracer quality information over the local area network.

4. The apparatus of claim 2, wherein the local area network is further operably coupled to a radioisotope producer and wherein the dispensing station receives the radioisotope from the radioisotope producer.

5. The apparatus of claim 4, wherein the radioisotope producer further comprises a cyclotron.

6. The apparatus of claim 4, wherein the radioisotope producer further comprises a linear accelerator.

7. The apparatus of claim 4, wherein the radioisotope producer further comprises a radioisotope generator.

8. The apparatus of claim 1, wherein the radiotracer further comprises nitrogen-13 ammonia.

9. The apparatus of claim 1, wherein the radiotracer further comprises fluorodeoxyglucose.

10. The apparatus of claim 1, wherein the imaging system further comprises a plurality of positron emission tomography imaging systems.

11. The apparatus of claim 1, wherein the imaging system further comprises:
a computer system having a graphical user interface operably coupled to the local area network;
an injector system to extract at least one individual dose from the radiotracer and to inject the at least one individual dose into the living subject, the injector system being operably coupled to the local area network; and
a physiologic monitoring system operably coupled to the injector system and operably coupled to the living subject.

12. The apparatus of claim 1, wherein the computer system calculates an amount of the individual dose based on the radioactive half-life of the radiotracer, the projected time of injection into a living subject and high level descriptors of the living subject.

13. The apparatus of claim 12, wherein the high level descriptors of the living subject further comprise the weight, sex and physical dimensions of the living subject.

14. The apparatus of claim 1, wherein the computer system calculates an amount of the individual dose based on a type of radiopharmaceutical, a predefined parametric equation, clinical protocol being followed and high level descriptors of the living subject, wherein the high level descriptors of the living subject further comprise the weight, sex and physical dimensions of the living subject.

15. The portable system of claim 1, wherein the computer system verifies an adequacy of the individual dose prior to injection.

16. The portable system of claim 1, wherein the computer system calculates a dosage for an individual dose based on at least one of a half-life of the pharmaceutical and a weight of the living subject.

17. The portable system of claim 1, wherein the dispensing station includes an extractor to extract the doses from the multi-dose container holding the multi-dose quantity, the dose calibrator to measure the radioactivity of the doses when extracted.

18. The portable system of claim 1, wherein the computer system calculates an individual dose based on at least one of a weight and sex of a living subject, wherein the dispensing station comprises an extractor that extracts the dose amount of the radiopharmaceutical that is reasonably expected to corresponding to the individual dose of the radiopharmaceutical.

19. The portable system of claim 1, wherein the computer system has a graphical user interface operably coupled to the dispensing station, the computer system recording the individual doses delivered to living subjects.

20. The portable system of claim 1, wherein the computer system has a graphical user interface operably coupled to the dispensing station, the computer system calculating an individual dose based on a weight of the living subject.

21. The portable system of claim 1, wherein the dispensing station comprises an extractor that extracts an amount of the radiopharmaceutical from the multidose container until the ion chamber measures an amount of extracted radioactivity that corresponds to a desired amount of dose radioactivity.

22. The portable system of claim 1, wherein the computer system stored at least one of dosing data and an initial dose activity at an initial time.

23. The portable system of claim 1, wherein the liquid transfer path includes tubing that is lead-shielded.

24. The portable system of claim 1, wherein the liquid transfer line is configured to be coupled to an injection apparatus to dispense individual doses of the radiopharmaceutical.

25. The portable system of claim 1, wherein the liquid transfer path includes a continuous fluid path through the ion chamber.

26. The portable system of claim 1, wherein the pump system directs the individual dose along the liquid transfer path in a single direction through the ion chamber.

27. The portable system of claim 1, wherein the computer system controls the pump system to extract an amount of the radiopharmaceutical from the multi-dose container into the ion chamber, wherein the amount extracted is reasonably calculated to provide the individual dose, the computer system to determine whether a radioactivity of the amount in the ion chamber corresponds to a requested amount of radioactivity.

28. The portable system of claim 1, wherein the computer system obtains a target dosage and determines whether the individual dose corresponds to the target dosage immediately prior to injection while in close proximity to a site of injection proximate the imaging system.

29. The portable system of claim 1, wherein the computer system calculates a target dosage for the individual dose based on at least one of a half-life of the pharmaceutical and a weight of the living subject, and compares a measurement from the ion chamber to the target dosage to determine whether the individual dose in the ion chamber is adequate.

30. The portable system of claim 1, wherein the liquid transfer path includes a liquid transfer line, wherein at least a portion of the liquid transfer line is located within the ion chamber.

31. The portable system of claim 1, wherein the liquid transfer path includes a liquid transfer line, wherein the liquid transfer line extends through the ion chamber between the ion chamber inlet and outlet.

32. The portable system of claim 1, wherein the pump system directs the individual dose in a single direction through the liquid transfer path.

33. A portable medical radiopharmaceutical administration system comprising:
- a dispensing station to receive a liquid radiopharmaceutical in quantities suitable for multiple doses of the radiopharmaceutical, and to dispense the radiopharmaceutical, the dispensing station having a pump system and a liquid transfer path that is in fluid communication with the liquid radiopharmaceutical;
- an ion chamber to measure radioactivity, the ion chamber having an ion chamber inlet, through which the liquid entering the ion chamber, and a separate ion chamber outlet, from which the liquid exits the ion chamber;
- a control system operably coupled to the dispensing station, the pump system to withdraw an individual dose from the multiple doses of the liquid radiopharmaceutical and move the individual dose along the liquid transfer path through the ion chamber inlet to the ion chamber, the ion chamber to measure a radioactivity of the individual dose in the ion chamber, the pump system to discharge the individual dose through the ion chamber outlet;
- a radioactivity shield that surrounds portions of the medical radiopharmaceutical administration system that are radioactive; and
- wheels mounted to the shield.

34. The portable medical radiopharmaceutical administration system of claim 33, wherein the portions of the system that are radioactive further comprise the dispensing station and the ion chamber.

35. The portable medical radiopharmaceutical administration system of claim 33, further comprising local area network operably coupled to the control system and a radioisotope producer and wherein the dispensing station receives the liquid radiopharmaceutical from the radioisotope producer.

36. The portable medical radiopharmaceutical administration system of claim 33, wherein the liquid transfer path includes a liquid transfer line, wherein at least a portion of the liquid transfer line is located within the ion chamber.

37. The portable medical radiopharmaceutical administration system of claim 33, wherein the liquid transfer path includes a liquid transfer line, wherein the liquid transfer line extends through the ion chamber between the ion chamber inlet and outlet.

38. The portable medical radiopharmaceutical administration system of claim 33, wherein the pump system directs the individual dose in a single direction through the ion chamber.

39. The portable medical radiopharmaceutical administration system of claim 33, wherein the radiopharmaceutical is selected from the group consisting of nitrogen-13, fluorine-18, carbon-11, oxygen-15 and rubidium-82.

40. The portable medical radiopharmaceutical administration system of claim 33, wherein each of the plurality of positron emission tomography imaging systems further comprises:
- a computer system having a graphical user interface operably coupled to the local area network;
- an injector system to extract at least one individual dose from the liquid radiopharmaceutical and to inject the at least one individual dose into the living subject, the injector system being operably coupled to the local area network; and
- a physiologic monitoring system operably coupled to the injector system and operably coupled to the living subject.

41. The portable medical radiopharmaceutical administration system of claim 40, wherein the amount of each individual dose is calculated based on type of radiopharmaceutical, a predefined parametric equation, clinical protocol being followed and high level descriptors of the living subject, wherein the high level descriptors of the living subject further comprise the weight, sex and physical dimensions of the living subject.

42. A medical radiopharmaceutical administration system comprising:
- a local area network operably coupled to a plurality of positron emission tomography imaging systems;
- a dispensing station to receive a nitrogen-13 ammonia in quantities suitable for multiple doses of the nitrogen-13 ammonia, and to dispense the nitrogen-13 ammonia to the plurality of positron emission tomography imaging systems, the dispensing station being operably coupled to the local area network;
- a quality control unit to monitor the amount of radiochemical and the radionuclic purity of the nitrogen-13 ammonia that is dispensed by the dispensing station, the quality control unit being operably coupled to the local area network to convey quality information over the local area network;
- a control system operably coupled to the local area network, to communicate with the plurality of positron emission tomography imaging systems, the dispensing station, and the quality control unit; and
- a plurality of delivery lines interconnected between the dispensing station and the plurality of PET imaging systems, the control system controlling dispensing of the individual doses over the delivery lines to the plurality of PET imaging systems.

43. The medical radiopharmaceutical administration system of claim 42, wherein the local area network is further operably coupled to a radioisotope producer selecting from the group consisting of a cyclotron, and a linear accelerator, and wherein the dispensing station receives the nitrogen-13 ammonia from the radioisotope producer.

44. The medical radiopharmaceutical administration system of claim 42, wherein the system further comprises being mounted on wheels.

45. The medical radiopharmaceutical administration system of claim 42, wherein the plurality of positron emission tomography imaging systems further comprises a plurality of positron emission tomography imaging systems, and wherein each of the plurality of positron emission tomography imaging systems further comprises:
- a computer system having a graphical user interface operably coupled to the local area network;
- an injector system to extract at least one individual dose from the nitrogen-13 ammonia and to inject the at least one individual dose into the living subject, the injector system being operably coupled to the local area network; and
- a physiologic monitoring system operably coupled to the injector system and operably coupled to the living subject.

46. The medical radiopharmaceutical administration system of claim 45, wherein the amount of each individual dose is calculated based on a predefined parametric equation, clinical protocol being followed and high level descriptors of the living subject, wherein the high level descriptors of the living subject further comprise the weight, sex and physical dimensions of the living subject.

47. A medical radiopharmaceutical administration system comprising:
- a local area network operably coupled to a plurality of positron emission tomography imaging systems;
- a dispensing station to receive liquid fluorodeoxyglucose in quantities suitable for multiple doses of the liquid fluorodeoxyglucose, and to dispense the fluorodeoxyglucose to the plurality of positron emission tomography imaging systems, the dispensing station being operably coupled to the local area network to send over the local area network information regarding the doses dispensed to the plurality of PET imaging systems;
- a control system operably coupled to the local area network, to receive status information from, and send commands to, the plurality of positron emission tomography imaging systems, the dispensing station, and the quality control unit; and
- a plurality of delivery lines interconnected between the dispensing station and the plurality of PET imaging systems, the control system controlling dispensing of the individual doses over the delivery lines to the plurality of PET imaging systems.

48. The medical radiopharmaceutical administration system of claim 47, wherein the local area network is further operably coupled to a cyclotron and wherein the dispensing station receives the liquid fluorodeoxyglucose.

49. The medical radiopharmaceutical administration system of claim 47, wherein the dispensing station is mounted on wheels.

50. The medical radiopharmaceutical administration system of claim 47, wherein the plurality of positron emission tomography imaging systems further comprises a plurality of positron emission tomography imaging systems, and wherein each of the plurality of positron emission tomography imaging systems further comprises:
- a computer system having a graphical user interface operably coupled to the local area network;
- an injector system to extract at least one individual dose from the liquid fluorodeoxyglucose and to inject the at least one individual dose into the living subject, the injector system being operably coupled to the local area network; and
- a physiologic monitoring system operably coupled to the injector system and operably coupled to the living subject.

51. The medical radiopharmaceutical administration system of claim 50, wherein the amount of each individual dose is calculated based on a predefined parametric equation, clinical protocol being followed and high level descriptors of the living subject, wherein the high level descriptors of the living subject further comprise the weight, sex and physical dimensions of the living subject.

52. A medical radiopharmaceutical administration system comprising:
- a local area network operably coupled to a plurality of positron emission tomography (PET) imaging systems;
- a dispensing station to receive a liquid radiotracer in quantities suitable for multiple doses of a radiopharmaceutical, and to dispense the radiopharmaceutical to the plurality of positron emission tomography imaging systems, the dispensing station being operably coupled to the local area network to send over the local area network information regarding the doses dispensed to the plurality of PET imaging systems;
- a quality control unit to monitor the amount of radio and the radionuclic purity of the radiopharmaceutical that is dispensed by the dispensing station, the quality control unit being operably coupled to the local area network and operably coupled to the dispensing station;
- a control system operably coupled to the local area network, to receive status information from, and send commands to, the plurality of positron emission tomography imaging systems, the dispensing station, and the quality control unit; and
- a plurality of delivery lines interconnected between the dispensing station and the plurality of PET imaging systems, the control system controlling dispensing of the individual doses over the delivery lines to the plurality of PET imaging systems.

53. The medical radiopharmaceutical administration system of claim 52, wherein the local area network is further operably coupled to a cyclotron and wherein the dispensing station receives the liquid radiopharmaceutical from the cyclotron.

54. The medical radiopharmaceutical administration system of claim 52, wherein the dispensing station is mounted on wheels.

55. The medical radiopharmaceutical administration system of claim 52, wherein a radioactivity shield surrounds portions of the system that are radioactive.

56. The medical radiopharmaceutical administration system of claim 52, wherein the radiotracer further comprises nitrogen-13 ammonia.

57. The medical radiopharmaceutical administration system of claim 52, wherein the radiotracer further comprises fluorodeoxyglucose.

58. The medical radiopharmaceutical administration system of claim 52, wherein each of the plurality of positron emission tomography imaging systems further comprises:
- a computer system having a graphical user interface operably coupled to the local area network;
- an injector system to extract at least one individual dose from the liquid radiopharmaceutical and to inject the at least one individual dose into the living subject, the injector system being operably coupled to the local area network; and a physiologic monitoring system operably coupled to the injector system and operably coupled to the living subject.

59. The medical radiopharmaceutical administration system of claim 58, wherein the amount of each individual dose is calculated based type of radiopharmaceutical, a predefined parametric equation, clinical protocol being followed and high level descriptors of the living subject.

60. The medical radiopharmaceutical administration system of claim 59, wherein the high level descriptors of the living subject further comprise the weight, sex and physical dimensions of the living subject.

61. The medical radiopharmaceutical administration system of claim 52, further comprising a chemical synthesizer operably coupled to the dispensing station, to receive a radioisotope, and to produce a radiotracer, and to transfer the radiotracer to the dispensing station.

62. A radiopharmaceutical administration system comprising:
a local area network operably coupled to a plurality of positron emission tomography (PET) imaging systems;
a dispensing station to receive a liquid radiopharmaceutical in quantities suitable for multiple doses of the radiopharmaceutical, and to dispense the radiopharmaceutical to the plurality of positron emission tomography imaging systems, the dispensing station being operably coupled to the local area network to send over the local area network information regarding the doses dispensed to the plurality of PET imaging systems;
a quality control unit, to monitor the amount of radiochemical and the radionuclic purity of the radiopharmaceutical that is dispensed by the dispensing station, the quality control unit being operably coupled to the local area network to send quality information over the local area network;
a control system operably coupled to the local area network, to receive status information from, and send commands to, the plurality of positron emission tomography imaging systems, the dispensing station, and the quality control unit; and
a plurality of delivery lines interconnected between the dispensing station and the plurality of PET imaging systems, the control system controlling dispensing of the individual doses over the delivery lines to the plurality of PET imaging systems;
wherein each of the plurality of positron emission tomography imaging systems further comprises:
a computer system having a graphical user interface operably coupled to the local area network;
an injector system to extract at least one individual dose from the liquid radiopharmaceutical and to inject the at least one individual dose into the living subject, the injector system being operably coupled to the local area network; and
a physiologic monitoring system operably coupled to the injector system and operably coupled to the living subject.

63. The radiopharmaceutical administration system of claim 62, wherein the local area network is further operably coupled to a cyclotron and wherein the dispensing station receives the liquid radiopharmaceutical from the cyclotron.

64. The radiopharmaceutical administration system of claim 62, wherein the dispensing station is mounted on wheels.

65. The radiopharmaceutical administration system of claim 62, wherein the radiotracer further comprises being selected from the group consisting of nitrogen-13 ammonia and fluorodeoxyglucose.

66. The radiopharmaceutical administration system of claim 62, wherein the amount of each individual dose is calculated based on type of radiopharmaceutical, a predefined parametric equation, clinical protocol being followed and high level descriptors of the living subject.

67. The radiopharmaceutical administration system of claim 66, wherein the high level descriptors of the living subject further comprise the weight, sex and physical dimensions of the living subject.

68. A medical radiopharmaceutical administration system comprising:
a local area network operably coupled to a plurality of positron emission tomography (PET) imaging systems;
a dispensing station to receive a liquid radiopharmaceutical in quantities suitable for multiple doses of the radiopharmaceutical, and to dispense the radiopharmaceutical to the plurality of positron emission tomography imaging systems, the dispensing station being operably coupled to the local area network to send over the local area network information regarding the doses dispensed to the plurality of Pet imaging systems;
a quality control unit, to monitor the amount of radiochemical and the radionuclic purity of the radiopharmaceutical that is dispensed by the dispensing station, the quality control unit being operably coupled to the local area network and operably coupled to the dispensing station;
a control system operably coupled to the local area network, to receive status information from, and send commands to, the plurality of positron emission tomography imaging systems, the dispensing station, and the quality control unit; and
a plurality of delivery lines interconnected between the dispensing station and the plurality of PET imaging systems, the control system controlling dispensing of the individual doses over the delivery lines to the plurality of PET imaging systems;
wherein each of the plurality of positron emission tomography imaging systems further comprises:
a computer system having a graphical user interface operably coupled to the local area network;
an injector system to extract at least one individual dose from the liquid radiopharmaceutical and to inject the at least one individual dose into the patient, the injector system being operably coupled to the local area network; and
a physiologic monitoring system operably coupled to the injector system and operably coupled to the patient.

69. The medical radiopharmaceutical administration system of claim 68, wherein the local area network is further operably coupled to a cyclotron and wherein the dispensing station receives the liquid radiopharmaceutical from the cyclotron.

70. The medical radiopharmaceutical administration system of claim 68, wherein the radiopharmaceutical is selected from a group consisting of nitrogen-13, fluorine-18, carbon-11, oxygen-15 and rubidium-82.

71. The medical radiopharmaceutical administration system of claim 68, wherein the amount of each individual dose is calculated based on type of radiopharmaceutical, a predefined parametric equation, clinical protocol being followed and high level descriptors of the patient, and wherein the high level descriptors of the patient further comprise the weight, sex and physical dimensions of the patient.

72. A system comprising:
  a local area network operably coupled to a plurality of positron emission tomography (PET) imaging systems;
  apparatus operable to dispense a radiopharmaceutical to the plurality of positron emission tomography (PET) imaging systems, the apparatus operable to dispense being operably coupled to the local area network to send over the local area network information regarding the doses dispensed to the plurality of PET imaging systems;
  apparatus operable to monitor the quality of the radiopharmaceutical that is dispensed by the apparatus operable to dispense, the apparatus operable to monitor being operably coupled to the local area network and operably coupled to the apparatus operable to dispense;
  apparatus operable to receive status information from the plurality of positron emission tomography imaging systems, the apparatus operable to dispense, and the apparatus operable to monitor, the apparatus operable to receive being operably coupled to the local area network;
  apparatus operable to send commands to the plurality of positron emission tomography imaging systems, the apparatus operable to dispense and the apparatus operable to monitor, the apparatus operable to send being operably coupled to the local area network; and
  a plurality of delivery lines interconnected between the dispensing station and the plurality of PET imaging systems, the apparatus operable to the individual doses over the delivery lines to the plurality of PET imaging systems.

73. An apparatus comprising:
  a computer system having a graphical user interface;
  a dispensing station operable to extract individual doses from a multidose vial of a radiopharmaceutical and dispense the individual doses to a plurality of positron emission tomography (PET) imaging systems;
  an injector operable to inject the individual doses into a patient, the injector system being operably coupled to the computer system; and
  a plurality of delivery lines interconnected between the dispensing station and the plurality of PET imaging systems, the computer system controlling dispensing of the individual doses over the delivery lines to the plurality of PET imaging systems.

74. The apparatus of claim 73, wherein the computer system receives data from the physiologic monitoring system, the injector system, a keyboard and the graphical user interface, and sends commands to the injector system.

75. The apparatus of claim 73, wherein the amount of each individual dose is calculated based on the radioactive half-life of the radiopharmaceutical, the projected time of injection into a living subject and high level descriptors of the patient.

76. The apparatus of claim 73, wherein the high level descriptors of the living subject further comprise the weight, sex and physical dimensions of the patient.

77. An imaging system comprising:
  an injector;
  a multi-dose container to hold a multi-dose quantity of liquid radiopharmaceutical;
  a dispensing station operable to extract individual doses of a radiopharmaceutical from the multi-dose container and distribute each individual dose to the injector and operably coupled to an imaging system, the dispensing station being mounted on wheels to be movable to and from the imaging system;
  an ion chamber to measure radioactivity therein, the ion chamber fluidly coupled to the dispensing station;
  a physiologic monitor operably coupled to the injector;
  an imaging scanner operably coupled to the physiologic monitor and the injector; and
  a computer system provided on the wheels, the computer system configured to calculate a target dosage for an individual dose based on at least one of a half-life of the pharmaceutical and a weight of the living subject, the computer system configured to control the dispensing station to withdraw an individual target dosage from the multi-dose container based on the target dosage and move the individual target dosage to the ion chamber, the ion chamber to measure a radioactivity of the individual target dosage in the ion chamber, the computer system configured to compare a measurement from the ion chamber to the target dosage to determine whether the individual target dosage in the ion chamber corresponds to the target dosage, the computer system configured to control the dispensing station to discharge the individual target dosage as an individual dose when the measurement from the ion chamber corresponds to the target dosage.

78. The imaging system of claim 77, wherein the injector is operable to inject individual doses of a radiopharmaceutical into a patient.

79. The imaging system of claim 77, wherein the radiotracer further comprises nitrogen-13 ammonia.

80. The imaging system of claim 77, wherein the radiotracer further comprises fluorodeoxyglucose.

81. The imaging system of claim 77, wherein the physiologic monitor is operably to monitor blood pressure and heart activity.

82. The imaging system of claim 77, wherein the operable coupling is provided by a local area network.

83. The imaging system of claim 77, wherein the computer system controls dispensing and injection of the individual dose of a radiopharmaceutical into the living subject and controls radiological scanning of the living subject.

84. A portable medical radiopharmaceutical administration system comprising:
  a moveable structure mounted on wheels to be moveable to and from an imaging system, the moveable structure including radioactivity shielding;
  a multi-dose container to hold a multi-dose quantity of liquid radiopharmaceutical;
  a dispensing station to receive the multi-dose container, the dispensing station having a pump system;
  an ion chamber to measure radioactivity therein, the ion chamber being fluidly coupled to the multi-dose container, wherein the multi-dose container, the dispensing station, and the ion chamber are enclosed within the radioactivity shielding while moved on the moveable structure to and from the imaging system; and
  a computer system provided on the moveable structure, the computer system configured to calculate a target dosage for an individual dose based on at least one of a half-life of the pharmaceutical and a weight of the living subject, the computer system configured to control the pump system to withdraw an individual target dosage from the multi-dose container based on the target dosage and move the individual target dosage to the ion chamber, the ion chamber to measure a radioactivity of the individual target dosage in the ion chamber, the computer system configured to compare a measurement from the ion chamber to the target dosage to determine whether the individual target dosage in the ion chamber corresponds to the target dosage, the computer system configured to control the pump system to discharge the individual target dosage as an individual dose when the measurement from the ion chamber corresponds to the target dosage.

85. The portable system of claim 84, further comprising a quality control unit provided within the radioactivity shielding on the moveable structure, the quality control unit being operably coupled to the dispensing station, the quality control unit monitoring a radioactivity of the liquid radiopharmaceutical prior to being dispensed by the dispensing station.

86. The portable system of claim 85, wherein the quality control unit monitors at least one of an amount, quality and quantity of the radioactivity.

87. The portable system of claim 85, wherein the quality control unit performs the monitoring at particular time intervals.

88. The portable system of claim 85, wherein the quality control unit performs the monitoring for a production batch of the radiopharmaceutical.

89. The portable system of claim 85, wherein the quality control unit calculates an amount of radioactivity based on at least one of a half-life of the radiopharmaceutical and an amount of time lapsed since production of the radiopharmaceutical.

90. The portable system of claim 84, further comprising a communications device provided on the moveable structure to communicate over a link with a remote computer, the communications device conveying at least one of status information, commands, dosage information, and dose production information.

* * * * *